United States Patent
Saito et al.

(10) Patent No.: US 9,046,521 B2
(45) Date of Patent: Jun. 2, 2015

(54) CANCER EVALUATION METHOD USING HAPTOGLOBIN β CHAIN DEFINED BY ANTIBODY RM2

(75) Inventors: Seiichi Saito, Miyagi (JP); Yoichi Arai, Miyagi (JP)

(73) Assignee: TOHOKU TECHNOARCH CO., LTD., Sendai-shi (JP)

( * ) Notice: Subject to any disclaimer, the term of this patent is extended or adjusted under 35 U.S.C. 154(b) by 812 days.

(21) Appl. No.: 12/669,691

(22) PCT Filed: Jul. 18, 2008

(86) PCT No.: PCT/JP2008/063467
§ 371 (c)(1),
(2), (4) Date: Jan. 19, 2010

(87) PCT Pub. No.: WO2009/011466
PCT Pub. Date: Jan. 22, 2009

(65) Prior Publication Data
US 2010/0173334 A1 Jul. 8, 2010

(30) Foreign Application Priority Data

Jul. 19, 2007 (JP) ................................. 2007-188516
Apr. 15, 2008 (JP) ................................. 2008-106074

(51) Int. Cl.
*G01N 33/574* (2006.01)

(52) U.S. Cl.
CPC .... *G01N 33/57434* (2013.01); *G01N 33/57407* (2013.01); *G01N 33/57438* (2013.01); *G01N 2333/805* (2013.01)

(58) Field of Classification Search
None
See application file for complete search history.

(56) References Cited

U.S. PATENT DOCUMENTS

2005/0221397 A1   10/2005   Saito

FOREIGN PATENT DOCUMENTS

WO   2005/098434 A2   10/2005
WO   2007/035576 A2   3/2007

OTHER PUBLICATIONS

Saito et al. Int. J. Cancer, 115:105-113, 2005.*
Fundamental Immunology, William E. Paul, M.D. ed., 3rd ed., p. 242, 1993.*
Kojima, M et al, "Urinary Tumor Marker", Medical Clinics of Japan, 1998, vol. 24, No. 11, pp. 2248-2251.
Uchida, T et al, "Tumor Markers in Renal Cell Carcinoma", Acta Urologica Japonica, 1986, vol. 32, No. 7, pp. 929-940.
Thompson, S et al, "Elevated Levels of Abnormally-Fucosylated Haptoglobins in Cancer Sera", British Journal of Cancer, 1987, vol. 56, No. 5, pp. 605-610.
Turner, G. A., "Haptoglobin: A Potential Reporter Molecule for Glycosylation Changes in Disease", Advances in Experimental Medicine and Biology, 1995, vol. 376, pp. 231-238.
Ang, I et al, "Study of Serum Haptoglobin and its Glycoforms in the Diagnosis of Hepatocellular Carcinoma: A Glycoproteomic Approach", Journal of Proteome Research, 2006, vol. 5, No. 10, pp. 2691-2700.
Thompson, S et al, "A Multiwell Lectin-Binding Assay Using *Lotus tetragonolobus* for Measuring Different Glycosylated Forms of Haptoglobin", Clinica Chimica Acta, 1989, vol. 180, No. 3, pp. 277-284.
Veronese, M et al, "The t(6;16) (p21;q22) Chromosome Translocation in the LNCap Prostate Carcinoma Cell Line Results in a tpc/hpr FusionGene", Cancer Research, Feb. 15, 1996, vol. 56, No. 4, pp. 728-732.
Fujimura, T et al, "Glycosylation Status of Haptoglobin in Sera of Patients with Prostate Cancer vs. Benign Prostate Disease of Normal Subjects", International Journal of Cancer, Sep. 5, 2009, vol. 122, pp. 39-49.
International Search Report of PCT/JP2008/063467, mailing date of Sep. 2, 2008.
Supplementary European Search Report dated Aug. 3, 2010, issued in corresponding European Patent Application No. 08791705.0.
Hasagawa, Yoko et al.; "Monoclonal Antibody RM2 as a New Tracer of Nuclear Imaging for Prostate Cancer" Journal of Urology, Lippincott Williams & Wilkins, Baltimore. MD, vol. 181, No. 4, Apr. 1, 2009, pp. 397.
Saito, Seiichi et al.,; "Haptoglobin-beta chain defined by monoclonal antibody RM2 as a novel serum marker for prostate cancer"; International Journal of Cancer, Aug. 1, 2008, vol. 123, No. 3, pp. 633-640, XP002591282.

* cited by examiner

*Primary Examiner* — Brad Duffy
(74) *Attorney, Agent, or Firm* — Westerman, Hattori, Daniels & Adrian, LLP

(57) ABSTRACT

The object of the present invention is to identify a molecule that is specifically recognized by antibody RM2 in tissue or serum of a cancer patient, and provide a method for diagnosing cancer in a simple manner with high specificity using the molecule as an indicator. The present method comprises evaluating a risk or grade of malignancy of genitourinary cancer in a subject using the level of the haptoglobin β chain to which antibody RM2 specifically binds or a fragment thereof in tissue or body fluid isolated from the subject as an indicator.

31 Claims, 22 Drawing Sheets

Fig. 3c gi|15319135|ref|XP_04 11 15 29.4% 347 38452 6.6

(XM_042641)) hypothetical protein XP_042641 [Homo sapiens] gi|15319142|ref|XP_054767.1| (XM_054767) hypothetical protein XP_054767 [Homo sapiens] gi|123507|sp|P00737|HPT1_HUMAN HAPTOGLOBIN-1 PRECURSOR gi|67586|pir||HPHU1 haptoglobin precursor, allele 1 - human gi|306880|gb|AAA52684.1| (X01763) preprohaptoglobin [Homo sapiens] gi|758097|emb|CAA52267.1| (X00637) haptoglobin alpha 1S [Homo sapiens]

gi|4826762|ref|NP_005 11 15 25.1% 406 45205 6.6

(NM_005143) haptoglobin [Homo sapiens] gi|4779267|ref|XP_042621.1| (XM_042621) haptoglobin [Homo sapiens] gi|123508|sp|P00738|HPT2_HUMAN HAPTOGLOBIN-2 PRECURSOR gi|67585|pir||HPHU2 haptoglobin precursor, allele 2 - human gi|31750|emb|CAA25137.1| (X00442) haptoglobin precursor [Homo sapiens] gi|292157|gb|AAA88078.1| (M69197) haptoglobin [Homo sapiens] gi|386783|gb|AAA68080.1| (K03431) haptoglobin [Homo sapiens] gi|458813|gb|AAA52665.1| (L29394) preprohaptoglobin [Homo sapiens]

| Filename | XCorr | DeltCN | ObsM+H+ | CalcM+H+ | SpR | SpScore | Ions% | # | Sequence | | |
|---|---|---|---|---|---|---|---|---|---|---|---|
| Feb27_RM24_02_375_383.2 | 3.202 | 0.3337 | 924.55 | 0.0 | 1 | 838.8 | 93.8% | 3 | R.ILGGHLDAK.G | 22 | (SEQ ID NO:3) |
| Feb27_RM24_02_638_642.2 | 2.5285 | 0.4661 | 920.95 | 0.0 | 1 | 580.6 | 85.2% | 1 | K.GSRPWQAK.N | 22 | (SEQ ID NO:4) |
| Feb27_RM24_02_1007_1012.2 | 3.3282 | 0.6154 | 1290.94 | 0.0 | 1 | 1534.4 | 86.4% | 1 | K.DIAPTLTLYVGK.K | 22 | (SEQ ID NO:5) |
| Feb27_RM24_02_897_902.2 | 2.9775 | 0.4251 | 1419.66 | 0.0 | 1 | 541.7 | 58.3% | 1 | K.DIAPTLTLYVGK.Q | 22 | (SEQ ID NO:6) |
| Feb27_RM24_02_488_468.1 | 2.0177 | 0.1785 | 858.59 | 0.0 | 1 | 123.9 | 83.3% | 1 | K.QLVEIEK.V | 11 | (SEQ ID NO:7) |
| Feb27_RM24_02_754_757.2 | 2.8039 | 0.4633 | 980.86 | 0.0 | 1 | 1135.0 | 87.5% | 1 | R.NGFVSGHGR.N | 2 | (SEQ ID NO:8) |
| Feb27_RM24_02_940_943.3 | 4.1811 | 0.488 | 1722.62 | 0.0 | 1 | 2703.4 | 59.6% | 3 | K.VVLHPNYSQVDIGLIK.R | 3 | (SEQ ID NO:9) |
| Feb27_RM24_02_915_924.2 | 3.9203 | 0.6135 | 1723.91 | 0.0 | 1 | 749.3 | 73.1% | 1 | K.VVMLPVADQDQC*IR.H | 2 | (SEQ ID NO:9) |
| Feb27_RM24_02_909_913.3 | 3.9161 | 0.5317 | 2187.28 | 0.0 | 1 | 877.4 | 36.8% | 1 | K.SPVGVQPILNEHTC*AGMSK.Y | 3 | (SEQ ID NO:10) |
| Feb27_RM24_02_759_762.2 | 4.2836 | 0.5871 | 1360.39 | 0.0 | 1 | 1521.1 | 86.4% | 1 | K.SCAVAEYGVYVK.V | 22 | (SEQ ID NO:11) |
| Feb27_RM24_02_803_808.2 | 3.7389 | 0.4142 | 1204.42 | 0.0 | 1 | 1173.1 | 88.9% | 1 | K.VTSIQDWVQK.T | 22 | (SEQ ID NO:12) |

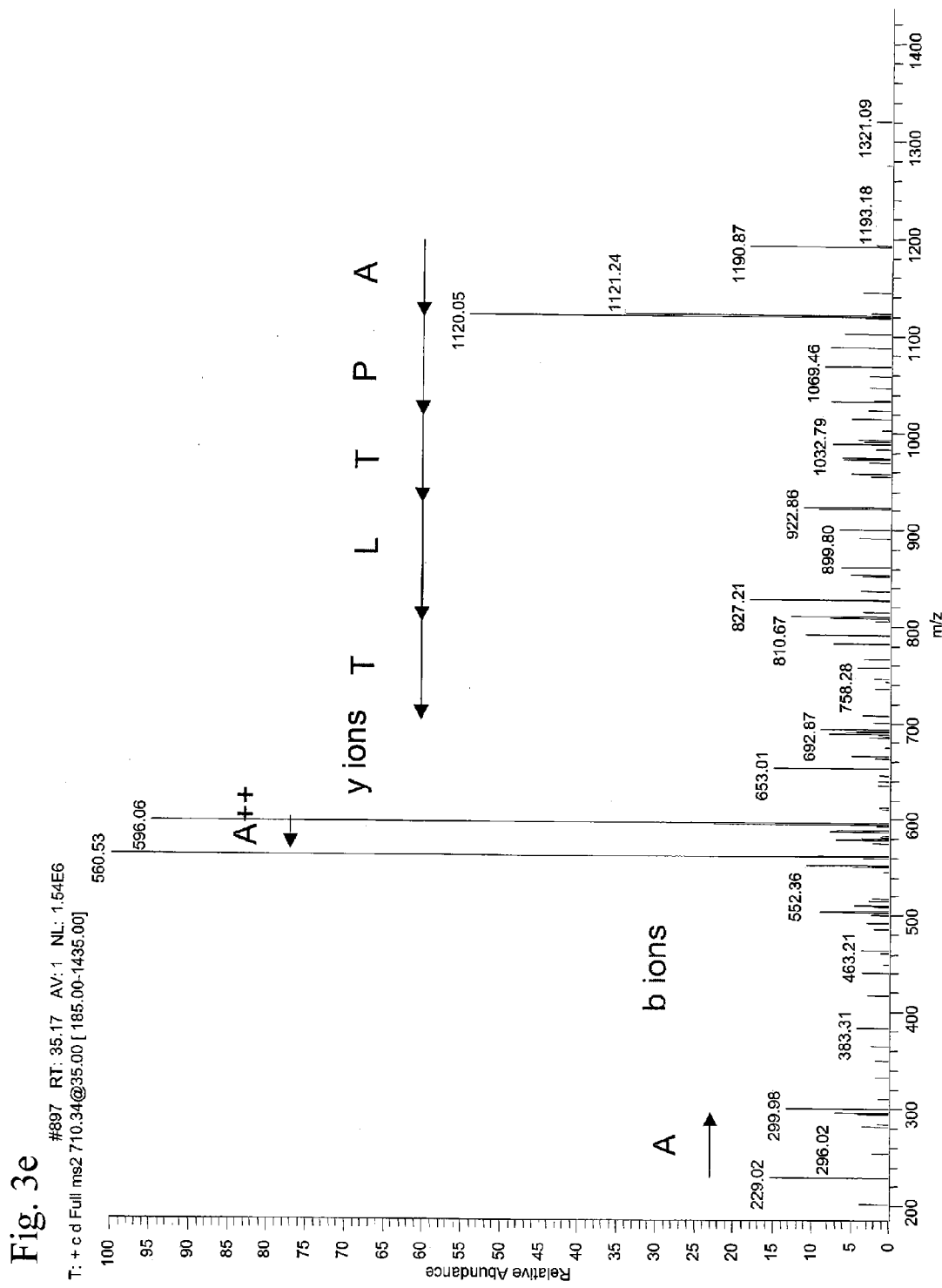

SEQUENCE LISTING

<160> NUMBER OF SEQ ID NOS: 12

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

```
Ser Cys Ala Val Ala Glu Tyr Gly Val Tyr Val Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic peptide

<400> SEQUENCE: 2

Asp Ile Ala Pro Thr Leu Thr Leu Tyr Val Gly Lys Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: partial peptide fragment of glycoprotein GPX

<400> SEQUENCE: 3

Arg Ile Leu Gly Gly His Leu Asp Ala Lys Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: partial peptide fragment of glycoprotein GPX

<400> SEQUENCE: 4

Lys Gly Ser Phe Pro Trp Gln Ala Lys Met
1               5                   10

<210> SEQ ID NO 5
<211> LENGTH: 14
<212> TYPE: PRT
<213> ORGANISM: Artificial Sequence
<220> FEATURE:
<223> OTHER INFORMATION: partial peptide fragment of glycoprotein GPX

<400> SEQUENCE: 5

Lys Asp Ile Ala Pro Thr Leu Thr Leu Tyr Val Gly Lys Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: partial peptide fragment of glycoprotein GPX

<400> SEQUENCE: 6

Lys Asp Ile Ala Pro Thr Leu Thr Leu Tyr Val Gly Lys Lys Gln
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: partial peptide fragment of glycoprotein GPX

<400> SEQUENCE: 7
```

```
Lys Gln Leu Val Glu Ile Glu Lys Val
1               5

<210> SEQ ID NO 8
<211> LENGTH: 11
<212> TYPE: PRT
<213> ORGANISM: Artificial Sequence
<220> FEATURE:
<223> OTHER INFORMATION: partial peptide fragment of glycoprotein GPX

<400> SEQUENCE: 8

Arg Val Gly Tyr Val Ser Gly Trp Gly Arg Asn
1               5                   10

<210> SEQ ID NO 9
<211> LENGTH: 16
<212> TYPE: PRT
<213> ORGANISM: Artificial Sequence
<220> FEATURE:
<223> OTHER INFORMATION: partial peptide fragment of glycoprotein GPX

<400> SEQUENCE: 9

Lys Tyr Val Met Leu Pro Val Ala Asp Gln Asp Gln Cys Ile Arg His
1               5                   10                  15

<210> SEQ ID NO 10
<211> LENGTH: 22
<212> TYPE: PRT
<213> ORGANISM: Artificial Sequence
<220> FEATURE:
<223> OTHER INFORMATION: partial peptide fragment of glycoprotein GPX

<400> SEQUENCE: 10

Lys Ser Pro Val Gly Val Gln Pro Ile Leu Asn Glu His Thr Phe Cys
1               5                   10                  15

Ala Gly Met Ser Lys Tyr
            20

<210> SEQ ID NO 11
<211> LENGTH: 14
<212> TYPE: PRT
<213> ORGANISM: Artificial Sequence
<220> FEATURE:
<223> OTHER INFORMATION: partial peptide fragment of glycoprotein GPX

<400> SEQUENCE: 11

Lys Ser Cys Ala Val Ala Glu Tyr Gly Val Tyr Val Lys Val
1               5                   10

<210> SEQ ID NO 12
<211> LENGTH: 12
<212> TYPE: PRT
<213> ORGANISM: Artificial Sequence
<220> FEATURE:
<223> OTHER INFORMATION: partial peptide fragment of glycoprotein GPX

<400> SEQUENCE: 12

Lys Val Thr Ser Ile Gln Asp Trp Val Gln Lys Thr
1               5                   10
```

CANCER EVALUATION METHOD USING HAPTOGLOBIN β CHAIN DEFINED BY ANTIBODY RM2

TECHNICAL FIELD

The present invention relates to a method for diagnosing cancer using the level of the haptoglobin β chain to which antibody RM2 specifically binds in tissue or body fluid isolated from a subject as an indicator. The hybridoma RM2 which produces the antibody RM2 was deposited under Accession No. FERM BP-11388 with International Patent Organism Depositary (IPOD), National Institute of Advanced Industrial Science and Technology (AIST), Tsukuba Central 6, 1-1-1 Higashi, Tsukuba, Ibaraki, Japan on Jun. 21, 2011.

BACKGROUND ART

To date, prostate-specific antigen (PSA) has been known as an early diagnostic marker for prostate cancer. However, PSA levels are elevated not only in case of prostate cancer but also in case of benign prostatic disease, and the specificity is insufficient. Accordingly, only 25% of males having PSA levels of 4 to 10 ng/ml are diagnosed as having cancer via a prostate gland biopsy. Further, it is pointed out recent years that prostate cancer is found in 15% of males having PSA levels of 4 ng/ml or less. Since PSA does not reflect the grade of malignancy, a pathological stage of prostate cancer cannot be predicted based on PSA alone. Accordingly, a novel diagnostic marker that compensates for or supplements the drawbacks of PSA is expected.

At present, serum protein profiling, serum anti-p53 antibody, serum caveolin-1, 50 KDa protein, and the like have been reported to be available for distinguishing prostate cancer from benign prostatic hyperplasia, IGFBP-2 and -3, IL-6 and IL-6sR, TGF-β1, urine MMP, and VEGF have been reported to be available for predicting the disease or prognosis of prostate cancer, and serum hK2 has been reported to be available for both thereof. As histological markers that are specific to the prostate gland, the aforementioned PSA and hK2 have been reported, as those that are specific to prostate cancer, DD3 is reported, and as those that are expressed in almost all prostate cancer cases, AMACR and Apolipoprotein-D have been reported. However, there has been no marker except for PSA that has been put to practical use in clinical settings as a serum marker used for deciding an indication of biopsy or evaluating the grade of malignancy. While EPCA-2, which is a serum marker assumed to be prostate-cancer-specific, was reported recent years, the target molecule of EPCA-2 antibody is deduced to be a nuclear matrix protein, although it has not yet been identified.

Under such circumstances, an antibody RM2-recognized antigen has drawn attention recent years (Saito S., et al., RM2 antigen (β1,4-GalNAc-disialyl-Lc4), "A Novel Carbohydrate Marker for Prostate Cancer," Biotherapy 20: 418-426, 2006). Antibody RM2 is a monoclonal antibody that is established so as to target novel ganglioside DSGb5 (disialosyl globopentaosylceramide) isolated from the disialoganglioside fraction extracted from renal cancer tissue. In the later research process, the antibody RM2-recognized antigen was found to be a novel sugar chain, β1,4-GalNAc-disialyl Lc4 (RM2 antigen), instead of DSGb5 (Saito S, Levery S B, Salyan M E K, et al: Common tetrasaccharide epitope NeuAcalpha2-3Galbeta1-3 (NeuAcalpha2-6) GalNAc, presented by different carrier glycosylceramides or O-linked peptides, is recognized by different antibodies and ligands having distinct specificities, J Biol Chem 269: 5644-5652, 1994; and Ito A, Levery S B, Saito S, et al: A novel ganglioside isolated from renal cell carcinoma. J Biol Chem 276: 16695-16703, 2001). Specifically, antibody RM2 was prepared by immunizing a mouse with a TOS-1 cell line derived from renal cancer having a disialoganglioside which has the same mobility as DSGb5 on thin layer chromatography. However, analysis of a sugar chain of the TOS-1 cell line, which was carried out at a later date, demonstrated that TOS-1 expressed RM2 antigen having the same mobility as DSGb5, instead of DSGb5 (Ito A, et al, 2001). Consequently, a sugar chain that would be recognized by the antibody became different from a sugar chain that was intended at the time of antibody preparation.

RM2 antigen has a very unique hybrid structure of a lacto-series type 1 sugar chain and ganglio-series sugar chain. It is known that a tumor marker CA19-9 for the digestive system having a lacto-series type 1 sugar chain is widely distributed in the epithelium and in the glands and that ganglio-series sugar chains are abundant in cells derived from the neuroectoderm. Accordingly, the present inventors expected expression of the RM2 antigen in prostate cancer, which is derived from the glandular epithelium and neuroendocrine differentiation was clinically observed in the case of prostate cancer. Thus, using antibody RM2, we inspected prostate cancer, which was subjected to radical prostatectomy. As a result, we discovered that antibody RM2 would reflect the grade of malignancy and react with prostate cancer and that the reactivity of antibody RM2 to benign glands was weak or negative (U.S. Patent Application No. 2005/0221397; Saito S, Egawa S, Endoh M, et al: RM2 antigen (beta-1,4-GalNAc-disialyl-Lc4) as a new marker for prostate cancer. Int J Cancer 115: 105-113, 2005). Samples of radical prostatectomy were formalin-fixed, and most glycolipids, such as gangliosides, were eluted. Thus, antibody RM2 was considered to react with a glycoprotein. However, whether or not RM2 antigen is expressed on a glycoprotein that reacts with antibody RM2 in prostate cancer tissue or serum of a prostate cancer patient was not confirmed, and a marker that is recognized by antibody RM2 was not identified.

SUMMARY OF THE INVENTION

The object of the present invention is to identify a molecule that is specifically recognized by antibody RM2 in tissue or serum of a cancer patient, and provide a method for diagnosing cancer in a simple manner with high specificity using the molecule as an indicator.

In order to attain the above object, the present inventors examined RM2 reaction levels in sera of patients with early prostate cancer and those with benign prostatic disease. Further, we attempted to identify a molecule to which antibody RM2 specifically reacts via proteomics analysis. As a result, we found that RM2 reaction levels in patients with early prostate cancer would significantly increase on a 40 kDa serum glycoprotein, compared with those of patients with benign prostatic disease.

We also confirmed that the 40 kDa glycoprotein is the haptoglobin β chain and qualitative changes involving structural changes in the haptoglobin β chain occur in cancer patients, in addition to quantitative changes. We also confirmed that reaction of antibody RM2 to the haptoglobin β chain was observed not only in prostate cancer but also in other genitourinary cancers.

The present invention has been completed based on the above findings. That is, the present invention relates to a method for evaluating a risk, prognosis (i.e., residual or recurrence of cancer), or grade of malignancy of genitourinary cancer in a subject comprising determining the level of the haptoglobin β chain to which antibody RM2 specifically binds or a fragment thereof in tissue, body fluid, or excretory substance (e.g., sputum or stools) isolated from the subject as an indicator.

According to the method of the present invention, antibody RM2 does not bind to the haptoglobin β chain or a fragment thereof via known β1,4-GalNAc-disialyl Lc4 as antigen RM2.

Examples of genitourinary cancers to be evaluated by the method of the present invention include prostate cancer, renal cancer, urothelial cancer (e.g., bladder cancer and cancer of the renal pelvis and ureter), and testicular cancer.

As tissue or body fluid samples, whole blood or serum is preferable in terms of convenience, although samples vary depending on a test method to be employed. In the case of urothelial cancer, a method involving determining the haptoglobin β chain in the urine is preferable.

The level of the haptoglobin β chain to which antibody RM2 specifically binds or a fragment thereof can be determined by, for example, mass spectrometry, such as SELDI-TOF-MS or MALDI-TOF-MS, or immunological techniques selected from solid phase immunoassay including Western blotting, dot blotting, slot blotting, ELISA, RIA, and modified techniques thereof (e.g., the sandwich method), and immunoprecipitation assay techniques.

A method involving SELDI-TOF-MS, MALDI-TOF-MS, or ELISA is herein described in detail as the preferable embodiment, from the viewpoint of convenience and treatment of multiple analytes.

The method of the present invention may further comprise determining other organ-specific cancer marker in combination. This enables evaluation with higher specificity regarding a given type of cancer. When prostate cancer is to be evaluated, for example, prostate cancer-specific antigen PSA can be used.

The present invention also provides a kit for evaluating genitourinary cancer that can be used for the evaluation method of the present invention. The kit comprises, as essential components, 1) antibody RM2, and 2) an anti-haptoglobin antibody.

Further, the kit may comprise other organ-specific marker, a secondary antibody necessary for detection, a reagent for detecting a labeled body, a protein chip, a reaction buffer, an enzyme, a substrate.

This description contains part or all of the contents as disclosed in the descriptions and/or drawings of Japanese Patent Application Nos. 2007-188516 (date of filing: Jul. 19, 2007) and 2008-106074 (date of filing: Apr. 15, 2008), based on which the present application claims a priority.

BRIEF DESCRIPTION OF THE DRAWINGS

FIG. 1b is a photograph showing the results of serum Western blotting using monoclonal antibody RM2 exhibiting increased RM2 reactivity to GPX in serum obtained from a patient with prostate cancer. Explanation regarding the symbols in FIG. 1b is as defined with regard to FIG. 1a.

The photographs shown in the lower left and right show the results of monoclonal antibody-based Western blot analysis of a protein component separated from the abovementioned fraction via two-dimensional electrophoresis. A band that is stained with antibody RM2 is clearly observed in specimen II-c, but no band is observed in specimen II-b.

Figure 3A:
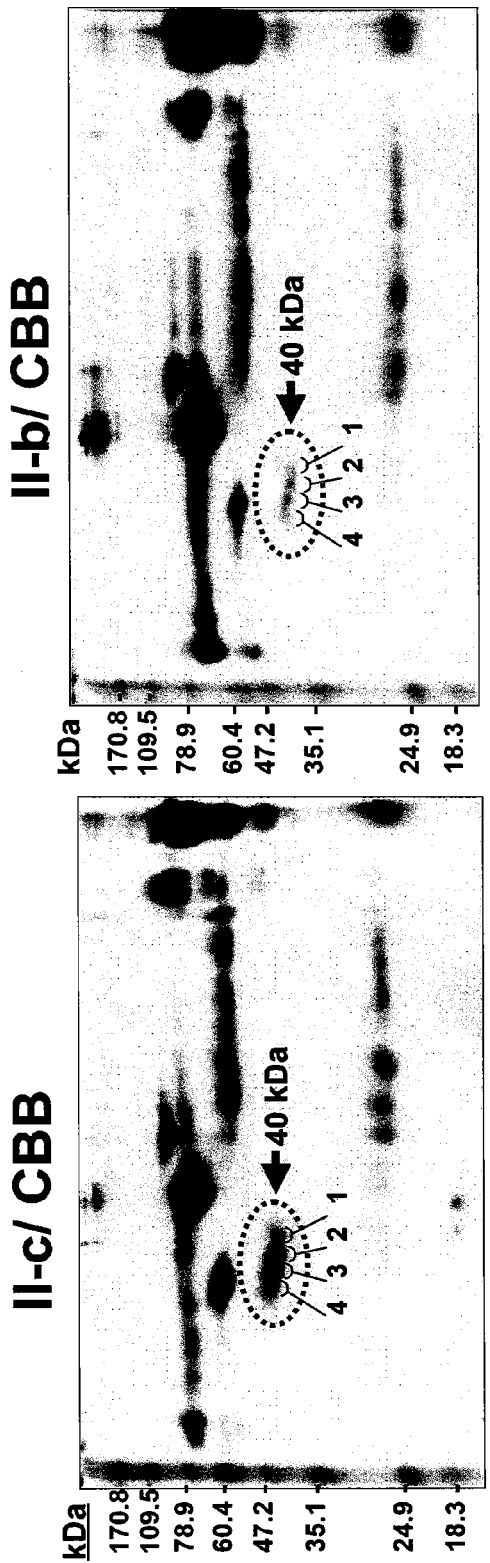
In FIG. 3a, the upper left and right photographs show images of fractions (fraction II) isolated from serum obtained from a patient with benign prostatic disease and from a patient with prostate cancer that had adsorbed to an Agilent column stained with Coomassie brilliant blue for the protein component isolated via two-dimensional electrophoresis; left: specimen II-c (fraction II of specimen c obtained from serum of a cancer patient); right: specimen II-b (fraction II of specimen b obtained from serum of a patient with benign disease); horizontal direction: isoelectric focusing; vertical direction: SDS-PAGE; the regions surrounded by dotted lines in both photographs are GPX. Specimen II-c (malignant) shows darker CBB staining than specimen II-b (benign). In each specimen, GPX is separated in 4 contiguous spots (1, 2, 3, and 4) having different isoelectric focusing patterns.
Figure 3A:
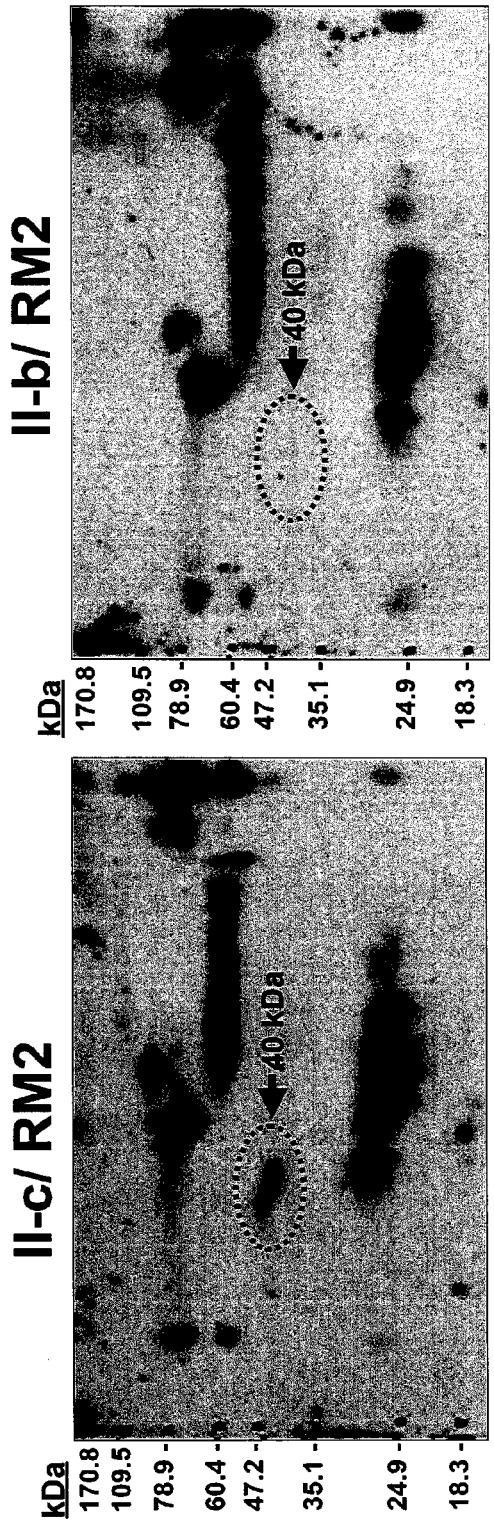
Figure 3B:
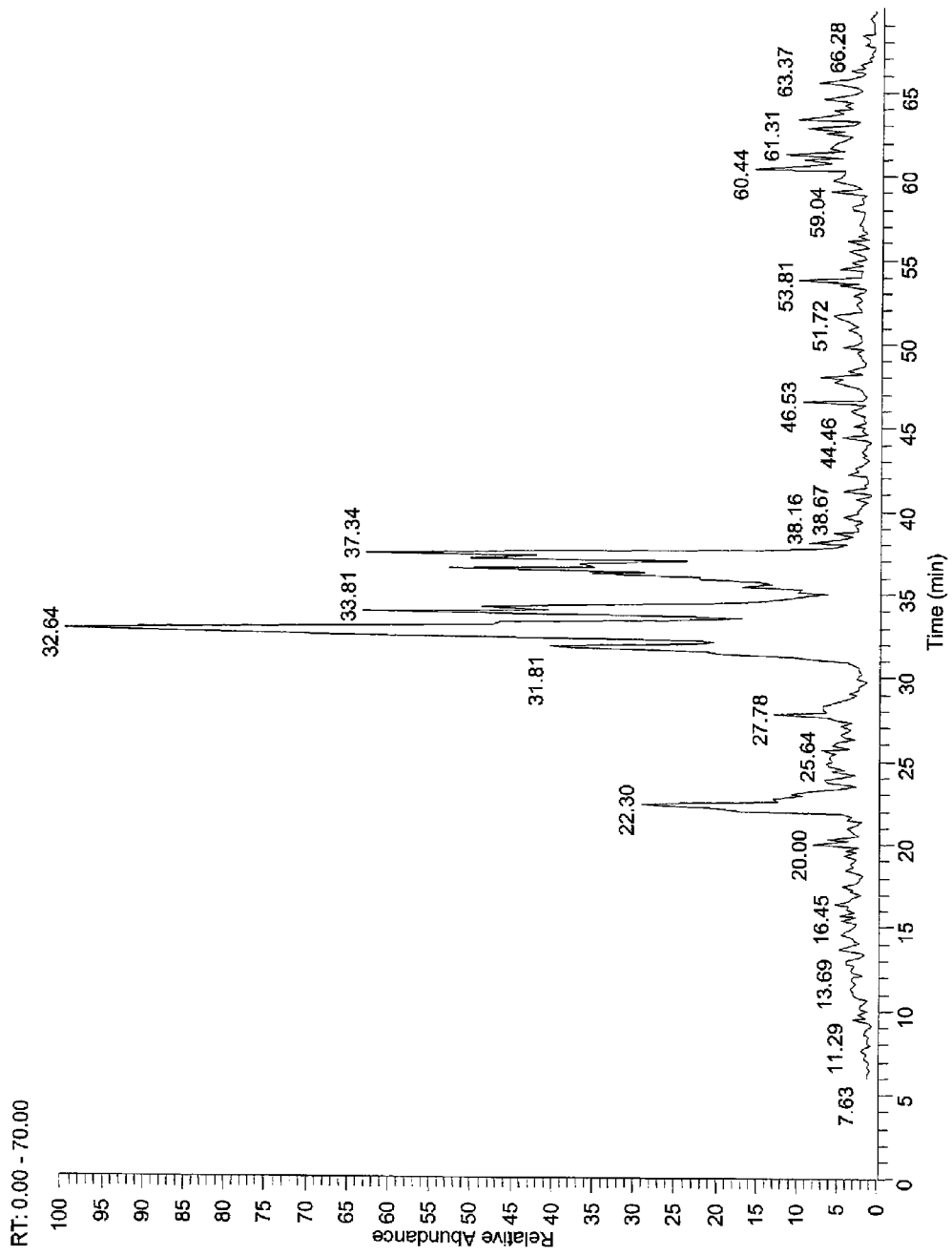

FIG. 3b shows a chromatogram obtained with the use of a liquid chromatography-mass spectrometry apparatus after extracting a peptide obtained by digesting spot 2 in FIG. 3a with trypsin in gel. The horizontal axis represents liquid chromatography retention time and the vertical axis represents the first mass spectrometry of the total ion chromatogram.

FIG. 3c shows the results of a data search via TurboSEQUEST, and shows SEQ ID NOs 3-12.

Figure 3D:
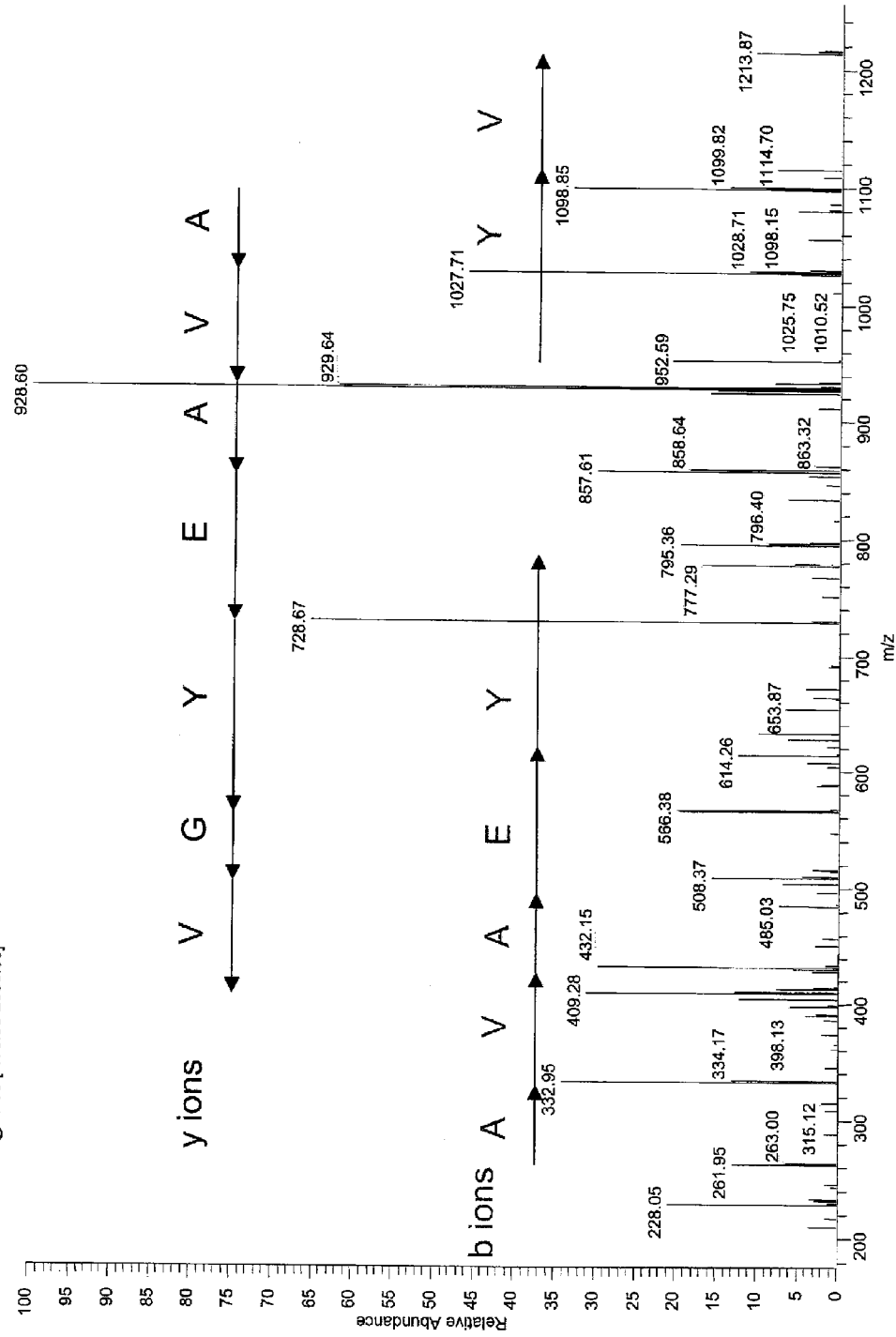

FIG. 3d shows the tandem mass spectra of a double-charged precursor ion at the mass-to-charge ratio of 680.

FIG. 3e shows the tandem mass spectra of a double-charged precursor ion at the mass-to-charge ratio of 710.

Figure 4A:
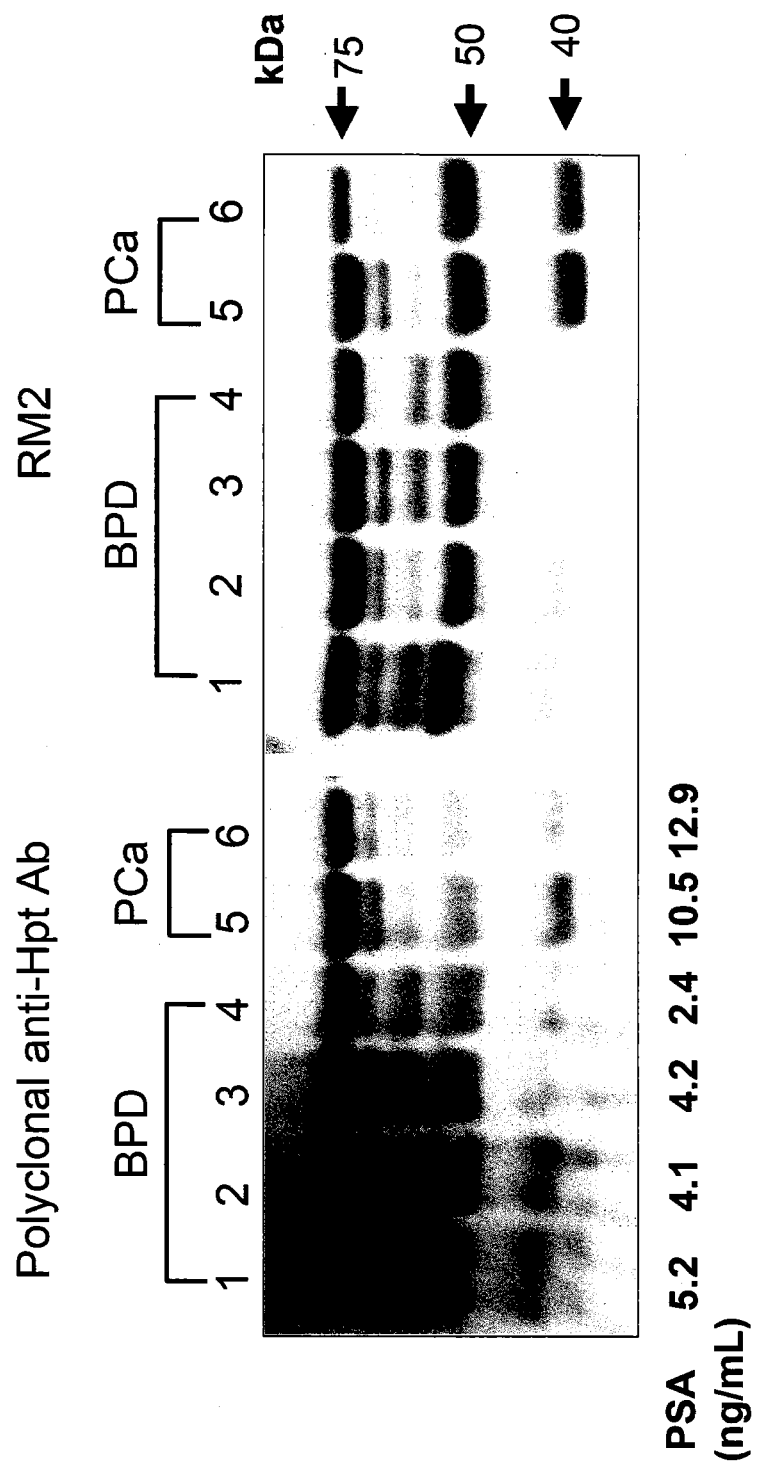

FIG. 4a is a photograph showing preferential reaction of antibody RM2 to the prostate cancer-derived haptoglobin β chain and an increase in the haptoglobin level in the prostate cancer cell. Examples of the reactions of the anti-haptoglobin polyclonal antibody and the antibody RM2 to sera obtained from patients with benign prostatic disease and those from patients with prostate cancer are shown. The left panel shows the reaction of the anti-haptoglobin polyclonal antibody to serum, the right panel shows the reaction of the antibody RM2 to serum, and the left panel and the right panel compare results for the same patients. The PSA level in each case is shown at the lower end. Hpt represents haptoglobin and Ab represents an antibody.

Figure 4B:
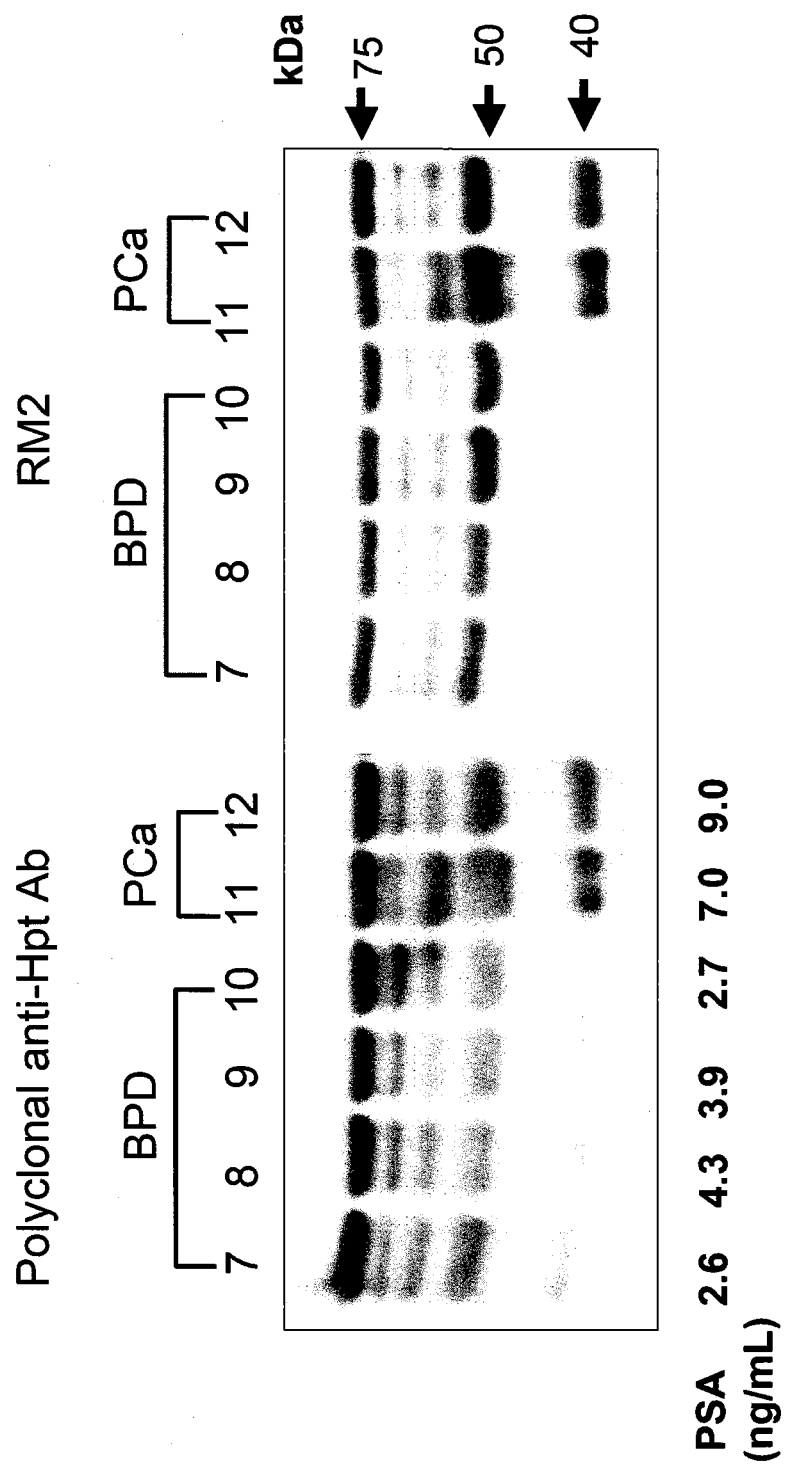

FIG. 4b is a photograph showing preferential reaction of antibody RM2 to the prostate cancer-derived haptoglobin β chain and an increase in the haptoglobin level in the prostate cancer cell. Examples of the reactions of the anti-haptoglobin polyclonal antibody and the antibody RM2 to sera obtained from patients with benign prostatic disease and those from patients with prostate cancer are shown. The description in FIG. 4a is employed herein.

Figure 4C:
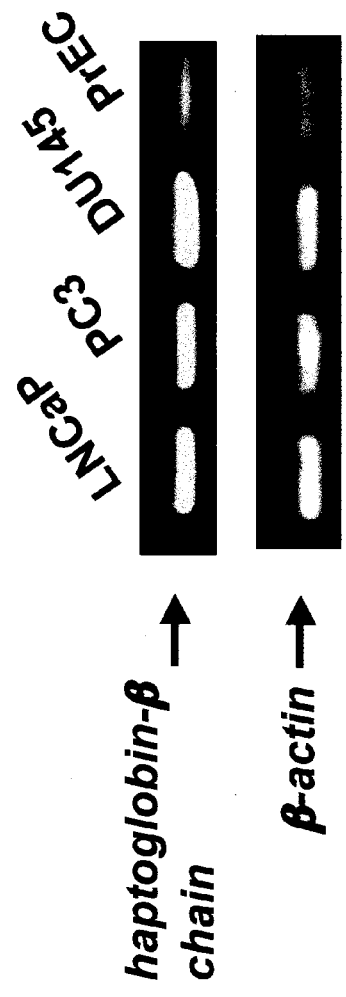
Figure 4C:
Figure 4C:

FIG. 4c is a photograph showing the haptoglobin expression level in the case of prostate cancer. The upper panel shows the mRNA level in the prostate cancer cell line, and the lower panel shows immunostaining of prostate cancer tissue with the anti-haptoglobin polyclonal antibody. Left: Gleason pattern 3; and right: Gleason pattern 4.

Figure 5:
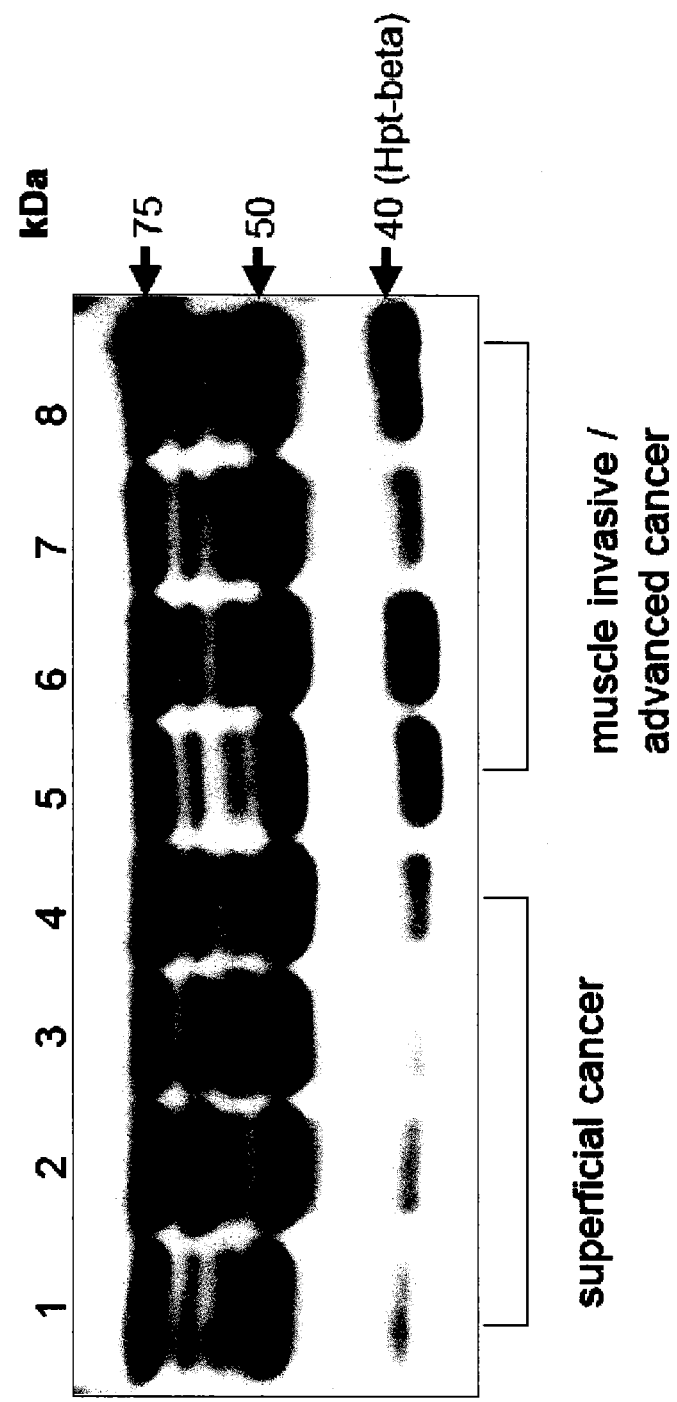

FIG. 5 is a photograph showing examples of reaction of antibody RM2 to sera of patients with bladder cancer. Superficial cancer; muscle invasive/advanced cancer.

Figure 6:
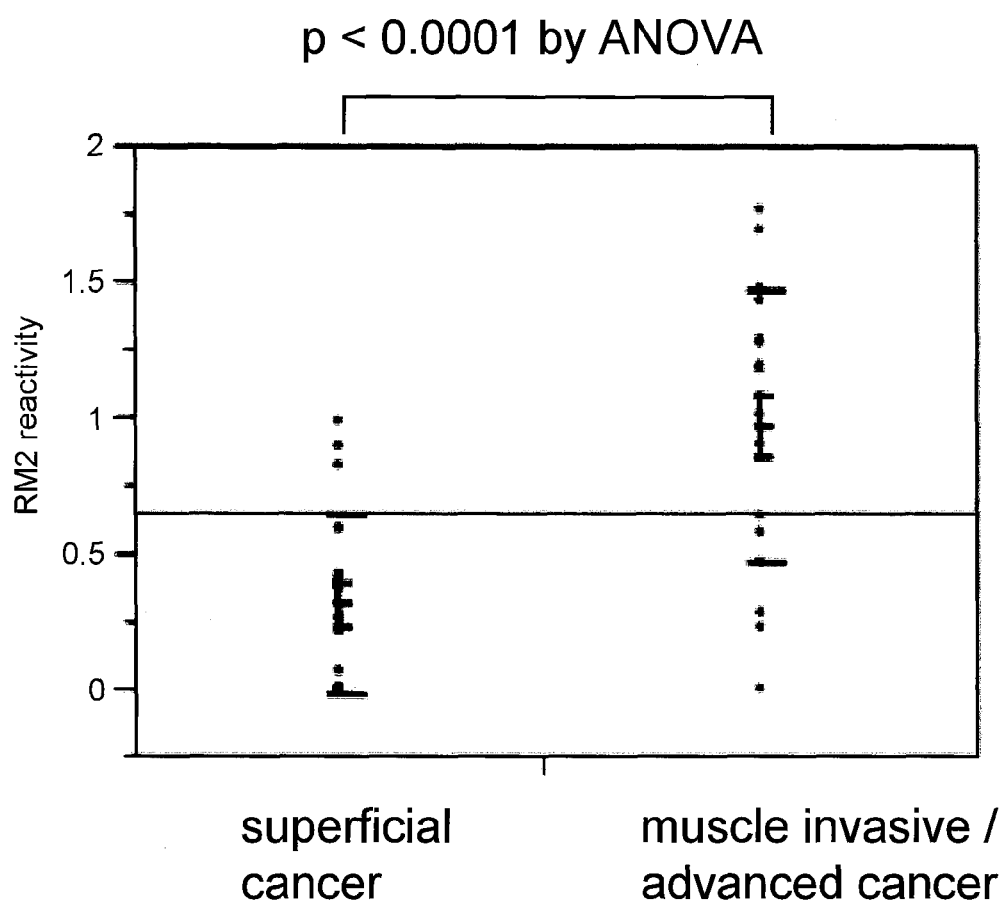

FIG. 6 is a chart showing a comparison of RM2 reaction to serum haptoglobin β chain between superficial cancer and muscle invasive/advanced cancer.

Figure 7:
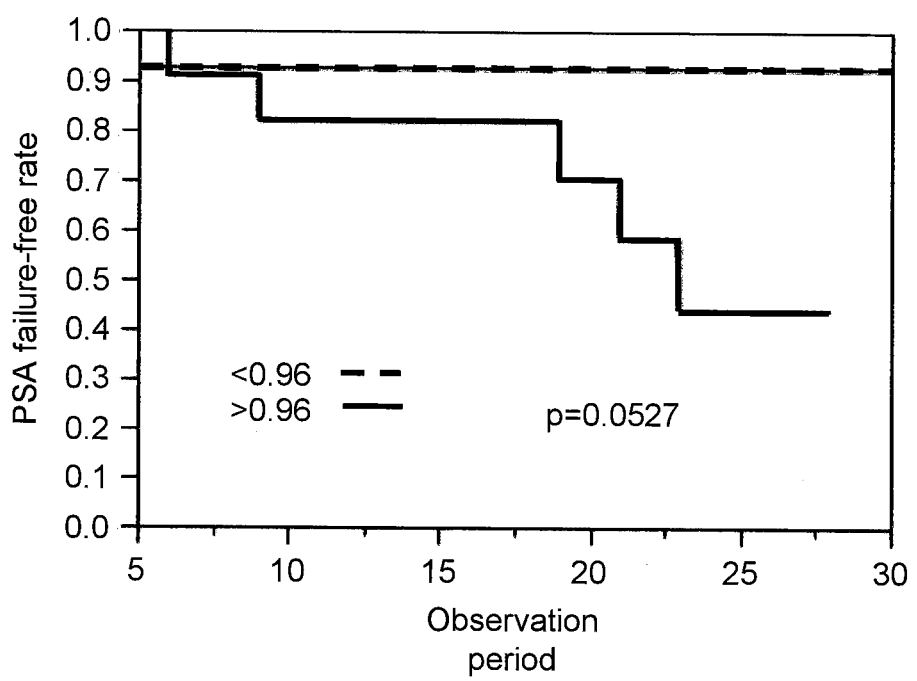

FIG. 7 is a chart showing the PSA non-recurrence rates depending on the serum levels of haptoglobin β chains defined by antibody RM2. The vertical axis represents the PSA non-recurrence rate and the horizontal axis represents the observation period (unit: month). The group exhibiting a high serum level of haptoglobin β chains defined by antibody RM2 (>0.96) exhibits a low rate of PSA non-recurrence after radical prostatectomy.

Figure 8:
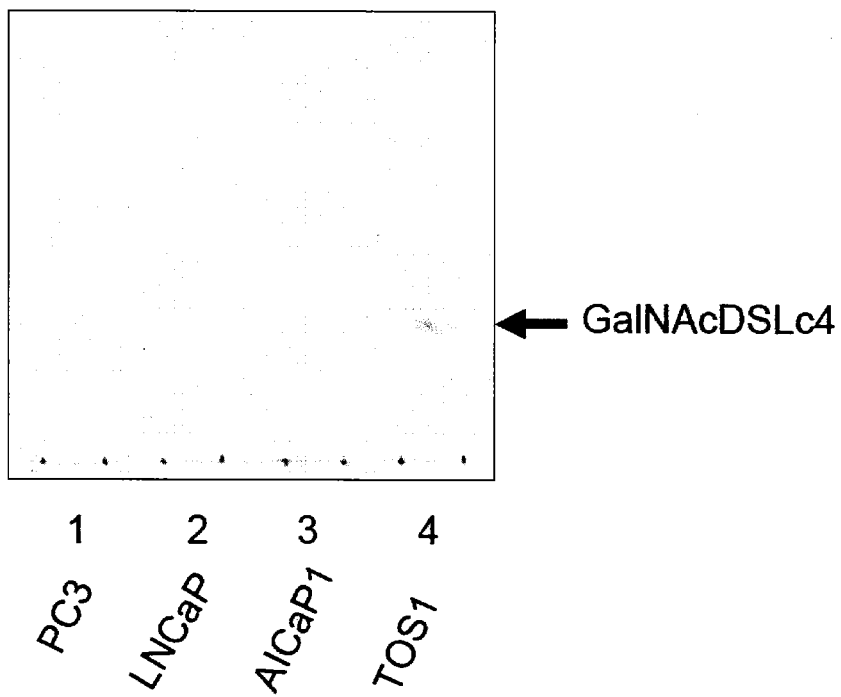

FIG. 8 is a photograph showing the results of evaluating the expression of a ganglioside, β1,4-GalNAc-disialyl Lc4(GalNAcDSLc4), which is recognized by antibody RM2 in the prostate cancer cell line. Lane 1: PC3; lane 2: LNCaP; lane 3: AICaP1 (an androgen-independent prostate cancer cell line that was newly established in the Department of Urology, Tohoku University School of Medicine); lane 4: TOS1 (a renal cancer cell line that was previously established in the Department of Urology, Tohoku University School of Medicine, used as a positive control for β1,4-GalNAc-disialyl Lc4).

Figure 9:
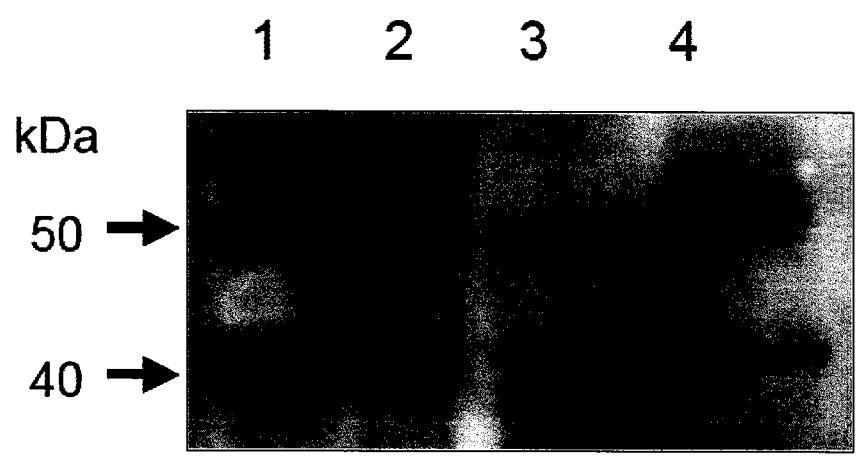

FIG. 9 is a photograph showing changes in RM2 reactivity to the protein extracted from the U145 cell by hemoglobin column treatment. Lane 1 shows untreated DU145 cell extract, lane 2 shows a fraction of the DU145 cell extract that had passed through the hemoglobin column without incubation, lane 3 shows a fraction of the DU145 cell extract that had passed through the hemoglobin column after incubation for 24 hours, and lane 4 shows a fraction eluted upon column washing, following step 3 (glycoprotein that had adsorbed to the column was eluted). An arrow indicates the molecular weight of the haptoglobin β chain (40 kDa) and that of the haptoglobin α- and β-chain complex (50 kDa).

Figure 10:
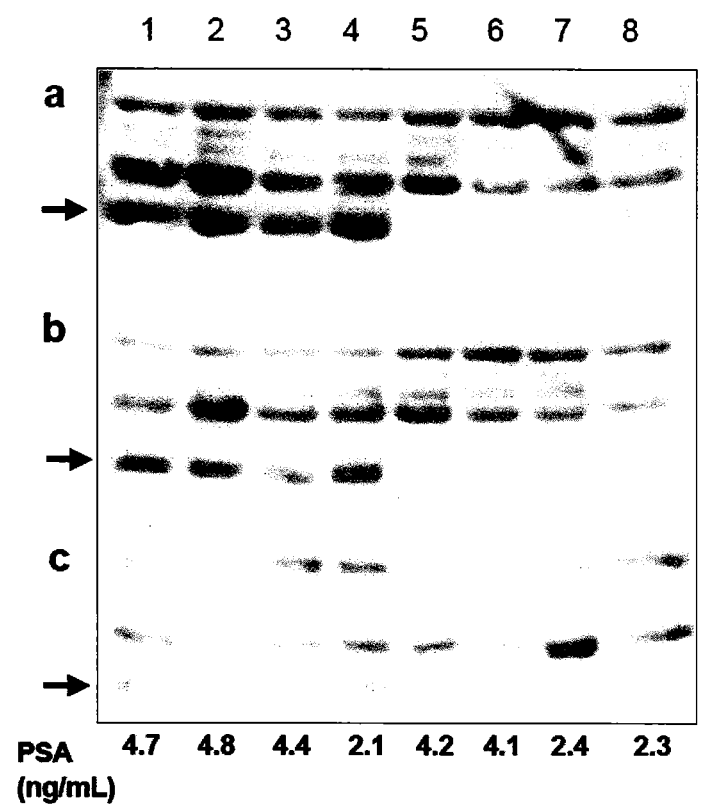

FIG. 10 is a photograph showing changes in RM2 reactivity to serum protein by glycolytic enzyme treatment. Lanes 1 to 4 show sera obtained from patients with prostate cancer and lanes 5 to 8 show sera obtained from patients with benign prostatic disease. "a" shows untreated serum, "b" shows serum treated with β-hexosaminidase from jack bean, and "c" shows serum treated with β-hexosaminidase, followed by sialidase from Newcastle disease virus.

Figure 11:
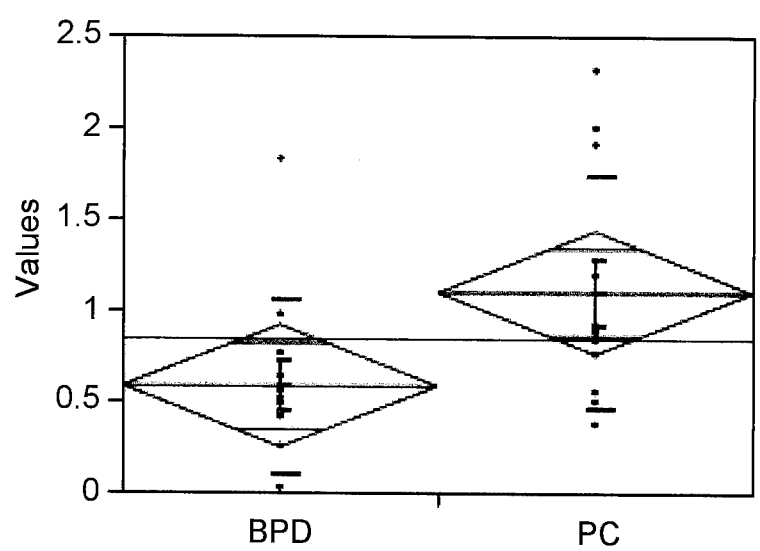

FIG. 11 is a chart showing the results of ELISA. In FIG. 11, "BPD" on the horizontal axis represents serum obtained from a patient with benign prostatic disease, "PC" represents serum obtained from a patient with prostate cancer, and value on the vertical axis represents the absorbance at 450 nm. While the average±the standard deviation value of the 12 measured samples of the patients with benign prostatic disease was 0.58±0.48, that of the 12 measured samples of the patients with prostate cancer was 1.1±0.64 (P=0.0352).

Figure 12:
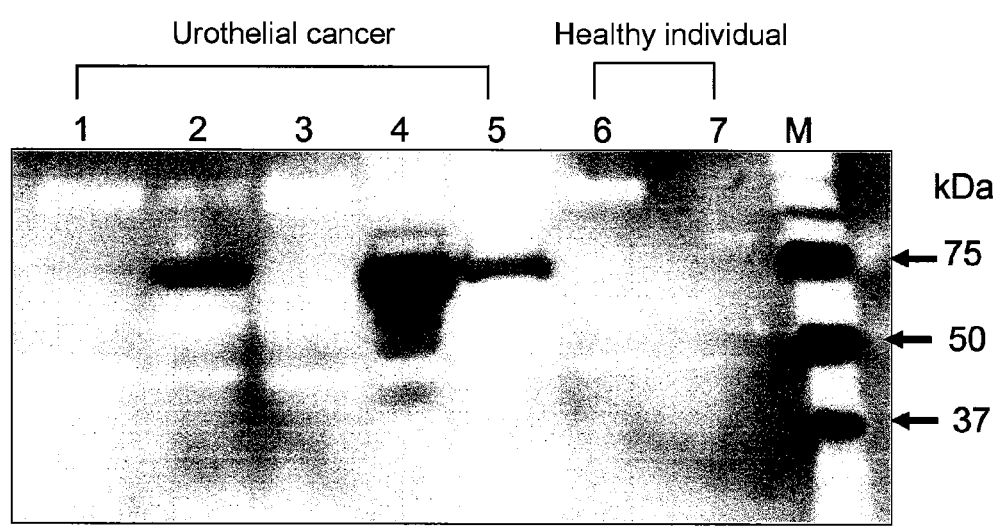

FIG. 12 is a photograph showing the results of Western blot analysis using antibody RM2 of the urine sample of a patient with urothelial cancer. Lanes 1 to 3 show the results for patients with bladder cancer, lanes 4 and 5 show the results for patients with renal pelvic cancer and bladder cancer, and lanes 6 and 7 show the results for healthy individuals. In 3 of 5 urothelial cancer cases, bands of about 75 kDa positive for antibody RM2 were detected. No reaction to antibody RM2 was observed in two healthy individuals.

BEST MODES FOR CARRYING OUT THE INVENTION

1. Definition

In the present invention, using the level of the haptoglobin β chain to which antibody RM2 specifically binds or a fragment thereof as an indicator, a risk, prognosis, or grade of malignancy of genitourinary cancer in a subject can be evaluated. Hereafter, terms according to the method of the present invention are described.

Antibody RM2

The term "antibody RM2" used herein refers to a monoclonal antibody established so as to target novel ganglioside DSGb5 (disialosyl globopentaosylceramide) isolated from renal cancer tissue, which was found to specifically recognize a novel sugar chain, β1,4-GalNAc-disialyl Lc4 later in the process of research.

Antibody RM2 can be prepared in accordance with a previous report (Saito S, et al., J. Biol. Chem. 269: 5644-5652, 1994) with the use of the renal cancer cell line, TOS1, as the immunogen.

The present inventors have already confirmed that antibody RM2 reacts with prostate cancer, it can be used as a histological marker to distinguish benign prostatic disease from prostate cancer, and reactivity thereof reflects the grade of malignancy of cancer. As described above, however, the reaction of antibody RM2 to prostate cancer was considered to result from recognition of RM2 antigen as a sugar chain, although a glycoprotein with which antibody RM2 would react with was unknown.

Haptoglobin β Chain

The term "haptoglobin β chain" used herein refers to a peptide chain constituting plasma glycoprotein haptoglobin. Haptoglobin is a plasma glycoprotein discovered by Polonovski in 1938, which specifically binds to hemoglobin. Haptoglobin is mainly produced in the liver (it was recently demonstrated that haptoglobin is produced from cancer), and it is composed of two large and small peptides of the α0 chain and the sugar-bound β chain, which are bound via SS-bonds. There are two types of α chains; i.e., α1 and α2, and there is one type of β chain. There are three genotypes; i.e., type 1-1, type 2-1, and type 2-2, depending on combination of these chains, and they correspond to proteins of Hp1-1 ((α1β)$_2$: molecular weight of about 100,000), Hp2-1 ((α1β)$_2$+(α2β)$_n$: molecular weight of about 200,000 or more), and Hp2-2 ((α2β)$_n$: molecular weight of about 400,000 or more). Recently, the correlation of the haptoglobin genotype and the susceptibility of developing a disease have been reported.

In clinical settings, haptoglobin is used to treat hemoglobinemia associated with hemolysis and hemoglobinuria. The haptoglobin level in the blood can be used to examine the presence of acute phase reactive substances or occurrence of hemolysis and to evaluate the degree of hepatopathy and incompatible blood transfusion. It is reported that haptoglobin is expressed at high levels in case of ovarian cancer, breast cancer, acute myelocytic leukemia, hepatocellular cancer, head and neck cancer, lung small cell cancer, and renal cancer. However, this constitutes merely a quantitative change of haptoglobin level, and does not involve qualitative change.

Human haptoglobin is considered to be mainly composed of Hp polymers; i.e., Hp2-1 and Hp2-2, having a molecular weight of about 430,000.

Haptoglobin β Chain to which Antibody RM2 Specifically Binds

The term "the haptoglobin β chain to which antibody RM2 specifically binds (antibody RM2-binding haptoglobin β chain)" used herein refers to the haptoglobin β chain to which antibody RM2 specifically recognizes and binds. In respect of reactivity of antibody RM2, such β chain is qualitatively and quantitatively distinguished from a normal haptoglobin β chain observed in healthy individuals.

"The haptoglobin β chain to which antibody RM2 specifically binds" is produced at a significantly high level in patients with prostate cancer, compared with patients with benign prostatic disease. Also, such β chain is produced at a significantly high level in patients with other genitourinary cancers. Specifically, in sera obtained from patients with genitourinary cancers, in addition to quantitative changes in haptoglobin levels, qualitative changes as seen in more preferential reaction of antibody RM2 to the haptoglobin β chain derived from sera of cancer patients (such reaction also being referred to as a "RM2 reaction" herein) are observed.

Since the present inventors could not verify that binding of antibody RM2 to the haptoglobin β chain was carried out via β1,4-GalNAc-disialyl Lc4, which had been known as RM2 antigen, we considered that the aforementioned binding was not achieved via β1,4-GalNAc-disialyl Lc4. At present, whether or not specific binding of antibody RM2 to the haptoglobin β chain results from a cross-reaction with another sugar chain or structural changes in the haptoglobin β chain has not yet been determined. However, it is apparent that "the haptoglobin β chain to which antibody RM2 specifically binds" can be used as a genitourinary cancer-specific marker.

In the present invention, a fragment of "the haptoglobin β chain to which antibody RM2 specifically binds" can also be encompassed, provided that antibody RM2 specifically binds thereto.

Genitourinary Cancer

As described above, cancers to be evaluated in the present invention are "genitourinary cancers." Examples thereof include prostate cancer, renal cancer, urothelial cancer (e.g., bladder cancer or cancer of the renal pelvis and ureter), and testicular cancer.

It should be noted that the aforementioned examples were actually verified by the present inventors in clinical settings and examples would not exclude the possibility of the use of "the haptoglobin β chain to which antibody RM2 specifically binds" as a marker for other cancers from the scope of the present invention. Since it is reported that haptoglobin is expressed at high levels in case of ovarian cancer, breast cancer, acute myelocytic leukemia, hepatocellular cancer, head and neck cancer, lung small cell cancer, and renal cancer and that the level of the fucosylated haptoglobin β chains is increased in case of pancreatic cancer, hepatocellular cancer, gastric cancer, and colon cancer, quantitative and qualitative changes in the levels of the haptoglobin β chain to which antibody RM2 specifically binds may also be observed in such cancers.

2. Method for Evaluating Cancer Using the Haptoglobin β Chain to which Antibody RM2 Specifically Binds as an Indicator 2.1: Sample Preparation The evaluation method of the present invention is carried out in a non-invasive manner with the use of tissue, peripheral blood (serum), body fluid such as urine or tissue extract, and excretory substances (e.g., sputum or stools) collected from the subject.

When the specimen is blood, insoluble blood cell components or the like are precipitated via centrifugation, serum is sampled, and the specimen is appropriately prepared in accordance with a method of subsequent detection.

A sample for ELISA/RIA (or a modified technique thereof) is prepared by appropriately diluting serum with a buffer. A sample for Western blotting (electrophoresis) is prepared by passing serum through a column (e.g., Aurum Serum Protein Mini Kit (Bio-Rad)) to remove albumin or IgG, appropriately diluting with a buffer, and mixing with a sample buffer (e.g., Sigma) containing 2-mercaptoethanol for SDS-polyacrylamide gel electrophoresis. A sample for dot/slot blotting is prepared by appropriately diluting serum with a buffer.

A sample for SELDI-TOF-MS or MALDI-TOF-MS is prepared by mixing serum and Urea buffer (under denaturing conditions) or PBS (under non-denaturing conditions) at a ratio of 1:9, diluting 10-fold with Binding/Washing buffer, and obtaining the supernatant. In the case of SELDI-TOF-MS, background noise can be significantly reduced with the use of an antibody RM2-coated protein chip. In the case of MALDI-TOF-MS, background noise can be significantly reduced with the use of a sample prepared by immunoprecipitating serum with antibody RM2 in advance. The target peak can be clearly detected as demonstrated by Western blotting.

2.2 Determination of the Haptoglobin β Chain to which Antibody RM2 Specifically Binds The results of Western blotting of the anti-haptoglobin polyclonal antibody and antibody RM2 demonstrated that antibody RM2 would more preferentially react with the cancer-derived haptoglobin β chain. This indicates that antibody RM2 recognizes qualitative differences between the haptoglobin chain derived from cancer and the haptoglobin β chain derived from benign disease. With the utilization of such specificity of antibody RM2, accordingly, cancer can be diagnosed with high sensitivity and high specificity.

The level of the antibody RM2-binding haptoglobin β chain to be used as an indicator can be determined via immunological techniques involving the use of antibody RM2 and the anti-haptoglobin antibody, or mass spectrometry involving the use of antibody RM2. The term "level" used herein refers to the amount of the antibody RM2-binding haptoglobin β chain, and also the term may refer to a titer (e.g., an antibody titer) that indirectly represents the amount. An anti-haptoglobin antibody may react with a sugar chain. In such a case, use of an anti-haptoglobin antibody that does not recognize the same site, which might be recognized by antibody RM2, is necessary. A monoclonal or polyclonal antibody may be used, and a commercially available antibody may be used.

Examples of mass spectrometry techniques that can be preferably employed include SELDI-TOF-MS and MALDI-TOF-MS. Examples of immunological techniques that can be employed include solid phase immunoassay or immunoprecipitation techniques, such as Western blotting, dot blotting, slot blotting, ELISA, and RIA (including modified techniques thereof such as the sandwich method).

Hereafter, preferable embodiments in terms of convenience and possibility for treatment of multiple analytes are described, although the present invention is not limited thereto.

(1) Mass Spectrometry

SELDI-TOF-MS

Surface-enhanced laser desorption/ionization (SELDI) comprises capturing given molecules that are present in a sample on a chip (e.g., a protein chip) using chemical functional groups or molecules fixed on the chip surface, purifying the molecules, and irradiating the purified molecules with laser beams to desorb and ionize the captured molecules. SELDI-TOF-MS analyzes such ionized molecules with the use of time-of-flight mass spectrometry (TOF-MS).

Specifically, a protein chip is coated with antibody RM2, incubated with a sample, and then washed. Subsequently, the chip on which the sample is mounted is irradiated with laser beams to perform mass spectrometry. Since the molecular weight of the haptoglobin β chain is known (40 kDa), patterns of serum samples of a benign prostatic disease or prostate cancer may be compared, so that a peak of interest that represents "the haptoglobin β chain to which antibody RM2 specifically binds" can be easily identified.

Such results may be compared with the data obtained when the chip is coated with the anti-haptoglobin polyclonal antibody, so as to facilitate diagnosis. This is because a stronger peak representing cancer is observed via antibody RM2 coating, while a peak representing a benign prostatic disease via antibody RM2 is equivalent to or weaker than the peak attained via polyclonal antibody coating.

Advantageously, SELDI-TOF-MS can simultaneously process many samples. Thus, SELDI-TOF-MS can be said to be excellent in terms of convenience, time, and cost.

MALDI-TOF-MS

Matrix assisted laser desorption/ionization (MALDI) comprises preparing a mixed crystal of a sample and a matrix, and irradiating the mixed crystal with laser beams to ionize the same. MALDI-TOF-MS analyzes such ionized molecules with the use of time-of-flight mass spectrometry (TOF-MS). Since a nitrogen laser (wavelength: 337 nm) or YAG laser (wavelength: 355 nm) is generally used as a laser source, a substance having an absorption band in such wavelength region is used as a matrix. Detection via MALDI-TOF-MS can be carried out by immunoprecipitating the sample (serum) with antibody RM2 in advance and performing SELDI-TOF-MS as described above.

(2) Immunological Technique

ELISA—ELISA Utilizing Size Fractionation

Serum sample is subjected to size fractionation with the use of a Nanosep centrifugal filter device to elute a fraction having a molecular weight of about 40 kDa. Subsequently, the eluate is divided into two aliquots and allowed to adsorb to a commercially available ELISA plate. The anti-haptoglobin polyclonal antibody and antibody RM2 are allowed to react with wells, and reaction intensities may be compared to detect the antibody RM2-binding haptoglobin β chain.

When the sandwich method is employed, the size-fractionated serum is added to the ELISA plate coated with antibody RM2. The plate is incubated, washed, and allowed to react with the anti-haptoglobin polyclonal antibody. Thus, prostate cancer can be distinguished from a benign prostatic disease.

According to the above method, detection is carried out by using a labeled antibody RM2 and a labeled anti-haptoglobin antibody. Examples of preferable labels include, but are not limited to, an enzyme (alkaline phosphatase or horseradish peroxidase) and biotin (a procedure of binding enzyme-labeled streptavidin to biotin as a secondary antibody is further necessary). As labeled secondary antibodies (or labeled streptavidin), various pre-labeled antibodies (or streptavidin) are commercially available. By detecting the activity of such labeled enzymes, the level of the antibody RM2-binding haptoglobin β chain can be determined. When labeling with alkaline phosphatase or horseradish peroxidase is intended, substrates that develop color or emit light with the aid of catalysts of such enzymes are commercially available.

Use of a color-developing substrate allows visual detection via Western blotting or dot/slot blotting. ELISA is preferably carried out with the use of a commercially available microplate reader to assay the absorption or fluorescent intensity of wells (detection wavelengths vary depending on substrate).

Use of a light-emitting substrate allows detection via autoradiography using an x-ray film or an imaging plate or photographing using an instant camera according to Western blotting or dot/slot blotting. Also, quantification with the utilization of densitometry, the Molecular Imager Fx System (BioRad), or the like can be carried out. When ELISA involves the use of a light-emitting substrate, enzyme activity is measured using a light-emitting microplate reader (e.g., a product of BioRad).

In the case of RIA, following size fractionation described above, for example, measurement is carried out with the use of an antibody labeled with a radioisotope, such as $^{125}$I, and with the use of a gamma counter.

Immunoprecipitation Technique

When detection is carried out via an immunoprecipitation technique, for example, a serum sample isolated from a subject is subjected to size fractionation, labeled antibody RM2 and/or anti-haptoglobin antibody is added, the resultant is allowed to stand, and a complex of the antibody RM2 and/or anti-haptoglobin antibody and the haptoglobin β chain is collected as a precipitate via centrifugation or other means. Fluorescence or radioactivity of the label used for the collected precipitate is measured to detect the RM2-binding haptoglobin β chain.

2.3 Determination and Evaluation

When the antibody RM2-binding haptoglobin β chain or a fragment thereof is detected in a sample isolated from a subject at a significantly higher level compared with a healthy individual (e.g., $p<0.05$), the subject can be evaluated as likely to develop genitourinary cancer. Also, changes in such level of a single subject may be observed to evaluate the grade of malignancy (progress) or prognosis (residual or recurrence of cancer) of cancer.

Method for Determining RM2 Level

Western blotting was carried out under semi-quantitative conditions. Specifically, the reaction of antibody RM2 to a 75-kDa protein shows substantially no differences between prostate cancer and a benign prostatic disease. Thus, the reaction of antibody RM2 to the haptoglobin β chain was normalized to the reaction of antibody RM2 to a 75-kDa protein (measured using a Scion image). As a result, the maximal value representing sensitivity—(1-specificity) was found to be 0.59 on a receiver operating characteristics (ROC) curve. When a value higher than 0.59 is attained, accordingly, prostate cancer can be diagnosed with high sensitivity and specificity. This indicates that similar evaluation can be made via SELDI-TOF-MS, MALDI-TOF-MS, or ELISA assay.

Further, establishment of a technique for isolating the cancer-derived haptoglobin chain as a reference substance enables mass spectrometry that is carried out in the same manner as in PSA, and the results can be represented by concrete numerical values.

Evaluation of Malignancy

Prostate cancer derived from a transformation zone with low grade of malignancy shows a significantly low haptoglobin β chain/75 kDa protein amount, although there are not many such cases. Accordingly, it may be used for evaluating the grade of malignancy.

RM2 reaction to serum of a patient with urothelial cancer is described in Example 2 below. The level of the haptoglobin β chain in serum of urothelial cancer that has invaded the muscle was significantly higher than that of superficial cancer that has not invaded the muscle. Thus, the level of the haptoglobin β chain to which antibody RM2 specifically binds is considered to be useful for evaluating the grade of malignancy or progress of urothelial cancer. The annotation states that a significant increase in the level is observed in advanced multiple lung metastasis cases in the case of testicular cancer. Thus, such level may be useful for evaluating the grade of malignancy or progress of various types of cancer, although it depends on cancer type.

3. Use in Combination with Organ-Specific Marker

As described above, expression of the haptoglobin β chain to which antibody RM2 specifically binds at high levels is specific for cancer (in particular, genitourinary cancers), although it is not specific for a given organ, such as the prostate gland. In order to perform specific diagnosis of the target cancer, accordingly, such expression level may be employed in combination with another organ-specific marker, so that a given type of cancer may be more accurately diagnosed.

In the case of prostate cancer, for example, PSA that has been heretofore used as a prostate cancer marker may be used in combination with the method of the present invention. This enables prostate cancer-specific diagnosis. In the case of testicular cancer, a diagnostic method involving the use of α-fetoprotein (AFP) or human chorionic gonadotropin-β (hCG-β) that have been heretofore used as markers has been established, in addition to palpation and imaging. Thus, it may be useful for assisting such markers.

At present, however, there is no organ-specific marker, such as PSA, used for prostate cancer, which is available for other types of cancer. Since cancer other than digestive tract cancer can be easily diagnosed via imaging such as an ultrasonograph or CT scanning, the haptoglobin β chain defined by antibody RM2 can be an excellent detection means for screening for cancer.

For example, renal cancer or urothelial cancer can be easily diagnosed via imaging such as CT scanning. In addition to urinary cancer, lung cancer, hepatic cancer, pancreatic cancer, or breast cancer (mammography) can be diagnosed via imaging. If a person is exposed to x-rays many times in order to find an early-stage cancer, such diagnostic method cannot be easily recommended from the viewpoint of secondary canceration or economic issues. However, use of the haptoglobin β chain to which antibody RM2 specifically binds enables application of imaging involving exposure selectively to patients who are in need thereof. Further, the haptoglobin β chain to which antibody RM2 specifically binds can be detected in early prostate cancer, and thus it can be an excellent means for discovering other early-stage cancers in the same manner.

4. Kit for Evaluating Cancer

The present invention also provides a kit for evaluating genitourinary cancer. The kit of the present invention comprises, as essential components, antibody RM2 and an anti-haptoglobin antibody.

The anti-haptoglobin antibody is not particularly limited, provided that the target antibody RM2-binding human haptoglobin β chain or a fragment thereof can be detected. A polyclonal or monoclonal antibody may be used. Although an antibody reacting with a human-derived haptoglobin β chain is preferable, an antibody reacting with a haptoglobin β chain derived from other species may be used, provided that the target antibody RM2-binding human haptoglobin β chain or a fragment thereof can be detected. When the kit is used for the sandwich method, another anti-haptoglobin antibody (other than antibody RM2) may react with a sugar chain. In such a case, use of an anti-haptoglobin antibody that does not recognize the same site, which might be recognized by antibody RM2, is necessary. A monoclonal or polyclonal antibody may be used, and a commercially available antibody may be used.

The antibody RM2 or the anti-haptoglobin antibody may be labeled with an appropriate label (e.g., an enzyme, radioactive, or fluorescent label), or it may be appropriately modified with biotin or the like. Also, the antibody RM2 or the anti-haptoglobin antibody may be immobilized on an appropriate support in accordance with a target detection method. Alternatively, the kit may comprise a support, so that the antibody can be immobilized thereon. Examples of supports that can be used include supports made of synthetic resin such as polyethylene, polypropylene, polybutyrene, polystyrene, polymethacrylate, or polyacrylamide to which proteins can be bound; glass, nitrocellulose, cellulose, and agarose supports; and gel-type supports. The form of a support is not particularly limited, and a support can be in the form of, for example, microparticles, such as microspheres or beads (e.g., "Latex" beads), a tube (inner wall) such as a microcentrifuge tube, or a microtiter plate (well).

When used in combination with a cancer marker specific for other organs, these markers may be contained in the kit.

In addition to the above components, the kit of the present invention may comprise other elements that are necessary for implementing the present invention, such as a secondary antibody, a reagent for detecting a labeled substance, a protein chip, a reaction buffer, an enzyme, a substrate, and the like, according to need.

Example 1

Increased Level of Haptoglobin β Chain to which Monoclonal Antibody RM2 Specifically Binds in Sera of Patients with Prostate Cancer 1. Subject and Method
(1) Serum Samples Serum samples of patients with prostate cancer or benign prostatic disease diagnosed via prostate gland biopsy and serum samples of patients with other genitourinary cancers were obtained from the Department of Urology, Tohoku University Hospital. The pathological staging (TNM) according to the 1997 system was employed, and the Gleason scores of all slides were diagnosed by a single pathologist.

(2) Cell Line

PC3, LNCaP, and DU145 were obtained from the Health Science Research Resources Bank. Normal human prostate gland epithelial cell PrEC was purchased from Cambrex Bioscience.

(3) Antibody

The monoclonal antibody RM2 was established in the following manner in accordance with the publication with the use of renal cancer cell line TOS1 as the immunogen (Saito S, et al., J. Biol. Chem., 269: 5644-5652, 1994). A polyclonal antibody against haptoglobin was purchased from Dako.

[Method for Obtaining Antibody RM2]

i) Preparation of Antigen Used for Screening for Monoclonal Antibody Reacting with Ganglioside Sugar chain antigens used for hybridoma screening were extracted in the following manner. Renal cancer cells/tissues obtained from a plurality of patients were subjected to extraction with 19 volumes of a mixed solution of chloroform/methanol (2:1), a mixed solution of chloroform/methanol (1:1), and a mixed solution of isopropanol/hexane/water (55:25:20), respectively, the extracted cells/tissues were mixed, and the mixture was concentrated to dryness with the use of a rotary evaporator. The extract was dissolved in 10 volumes of a chloroform/methanol mixed solution (2:1) relative to the volume of original cancer tissues, water was added thereto in an amount of ⅙ of the solution, and the resultant was subjected to Folch partition. Subsequently, the theoretical upper phases were collected, a mixed solution of chloroform/methanol/0.1% aqueous NaCl solution (1:10:10) was added to obtain the original volume (before collection), and the Folch partition was carried out three times. The upper phases were combined, concentrated to 10 ml with the use of an evaporator, and then dialyzed against distilled water at 4° C. for 3 days. The dialyzed solution was concentrated with the use of a rotary evaporator, followed by lyophilization. The resulting lyophilization product was dissolved in a small amount of a mixed solution of chloroform/methanol/water (30:60:8) and applied to DEAE-Sephadex A-25 equilibrated with the same solvent. A ganglioside fraction was eluted with a mixed solution of chloroform/methanol/0.5M aqueous sodium acetate solution (30:60:8), and the resultant was dialyzed against distilled water at 4° C. for 3 days, followed by lyophilization. The resulting lyophilization product was dissolved in a small amount of a mixed solution of chloroform/methanol (2:1), mounted on a high-resolution thin-layer chromatography plate (Merck), and developed with the aid of a mixed solution of chloroform/methanol/0.05% aqueous $CaCl_2$ solution (50:40:10). Thereafter, the ganglioside fraction was detected with the use of a 80% aqueous acetone solution containing 0.01% primulin (Aldrich) and via UV application. After the positions of ganglioside fractions (i.e., the monosialoganglioside fraction and the disialoganglioside fraction) containing 1 and 2 sialic acid(s) in its structure were confirmed, silica gel fractions on the thin-layer chromatography plate containing the ganglioside fractions were separately scraped therefrom with UV application, and the gel fractions were transferred to a test tube. A mixed solution of isopropanol/hexane/water (55:25:20) was added thereto, and ganglioside was extracted by ultrasonication. Such procedure was repeated three times in total and extracts were combined, concentrated, and lyophilized. The resulting extracts were refrigerated in a dried state before use.

ii) Immunization of Animal and Preparation of Hybridoma

The renal cancer cell line TOS1 (1 to $2 \times 10^7$ cells) was suspended in PBS, and the resulting suspension was injected intraperitoneally into a BALB/C mouse. Booster immunization was carried out 14 days later with the use of the same amount of a suspension, and the final immunization was carried out on the 35 day. The mouse spleen was removed 3 days thereafter, and spleen cells and the mouse myeloma cell line NS1 were subjected to cell fusion in accordance with a conventional technique to obtain hybridomas.

iii) Screening of Antibody RM2-Producing Hybridoma

Hybridomas were screened by evaluating the reactivity of the hybridoma culture supernatant to antigen RM2 via ELISA. Specifically, the monosialoganglioside fraction and the disialoganglioside fraction prepared in the above manner were added to separate ELISA plates at 10 ng/well, and fixed, and the hybridoma culture supernatant was allowed to react therewith. The reactivity to antigens was evaluated via ELISA. The reactivity was detected using the enzyme-labeled anti-mouse immunoglobulin antibody, and hybridomas that selectively reacted with the disialoganglioside fraction but did not react with the monosialoganglioside fraction were subjected to limiting dilution repeatedly to prepare monoclonal antibodies.

(4) Western Blotting of Serum

After IgG and albumin were removed using the Aurum Serum Protein Mini Kit (Bio-Rad), 20 µl of serum was electrophoresed on 10% SDS-PAGE, and transferred onto Hybond P PVDF membrane. The density of the reaction of antibody RM2 to a glycoprotein having a molecular weight of 40 kDa (GPX) in serum was assayed using Scion image, and the measured value of a glycoprotein having a molecular weight of 40 kDa (GPX) was normalized to the measured value of a glycoprotein having a molecular weight of 75 kDa from the same lane.

(5) Pretreatment of Serum Using Agilent Column and Two-Dimensional Electrophoresis Agilent Multiple Affinity Removal System column adsorbs 98% to 99% of 6 types of abundant proteins in human serum (i.e., albumin, immunoglobulins IgG and IgA, transferin, haptoglobin, and antitrypsin). The column and solutions A and B used for adsorption and elution were purchased from Agilent Technologies. Two-dimensional electrophoresis, alkylation, Western blotting, and gel digestion were carried out as described previously.

(6) Protein Identification

A trypsin digest was analyzed using 110-capillary HPLC (high-performance liquid chromatography) combined with a mass spectrometer of Agilent Technologies. The data were obtained by searching NCBI human sequence database using TurboSEQUEST.

(7) mRNA Level of Haptoglobin β Chain

Total RNA was extracted from PC3, LNCaP, DU145, and PrEC using Trizol reagent. Total RNA was reverse-transcribed into first-strand cDNA using ExScript reverse transcription kit. PCR was carried out using primers for the haptoglobin β chain and β actin.

(8) Immunostaining of Prostate Cancer Tissue with Anti-Haptoglobin Polyclonal Antibody Since there is no antibody specific for the haptoglobin β chain, an anti-human haptoglobin polyclonal antibody was used. Among the aforementioned radical prostatectomy samples, 20 samples were immunostained with the anti-haptoglobin polyclonal antibody.

(9) Statistical Analysis

Statistical analysis was carried out using the software from SAS Institute.

Figure 1A:
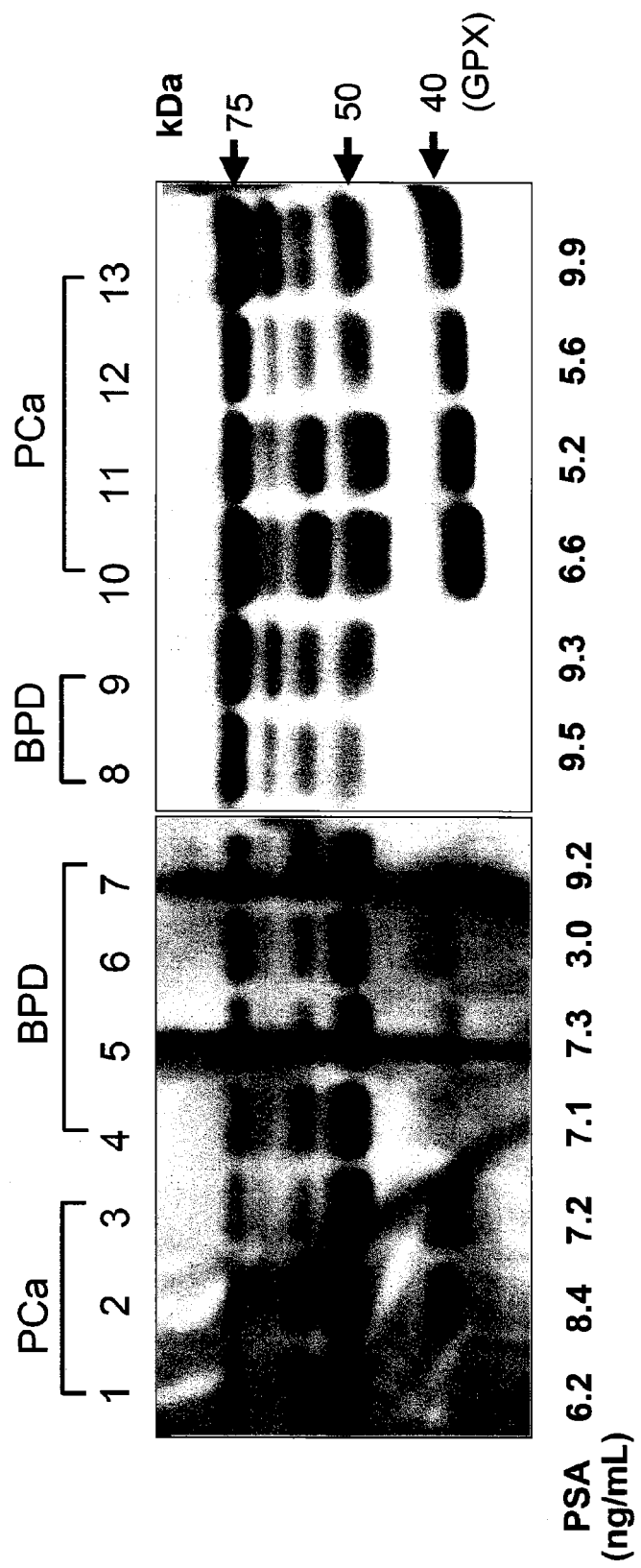
FIG. 1a is a photograph showing the results of serum Western blotting using monoclonal antibody RM2 exhibiting increased RM2 reactivity to GPX (i.e., serum glycoprotein having a molecular weight of 40 kDa) in serum obtained from a patient with prostate cancer. In the figure, PCa represents prostate cancer and BPD represents a benign prostatic disease. An arrow (→) indicates a position of a size marker or GPX. The PSA level of the sample is shown at the lower end of each panel.
Figure 1B:
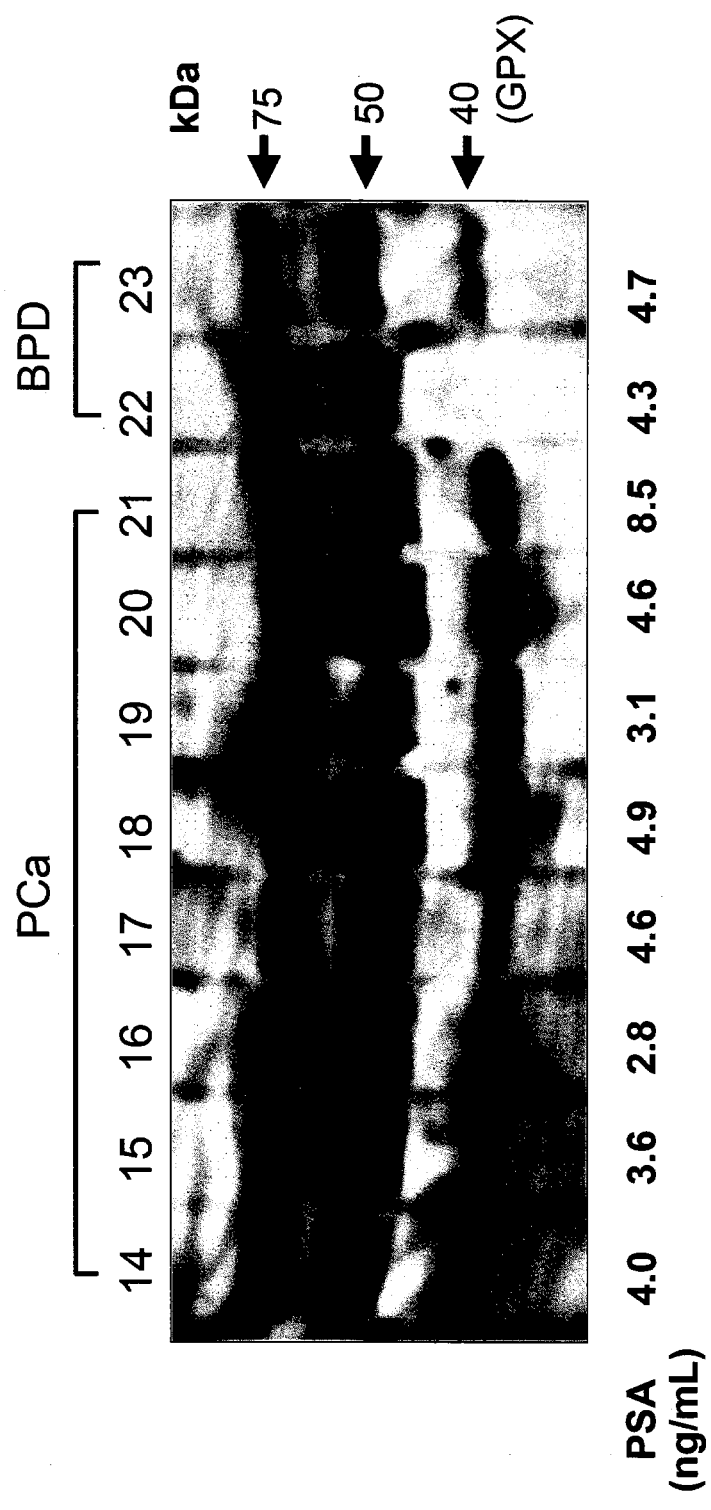
Figure 1C:
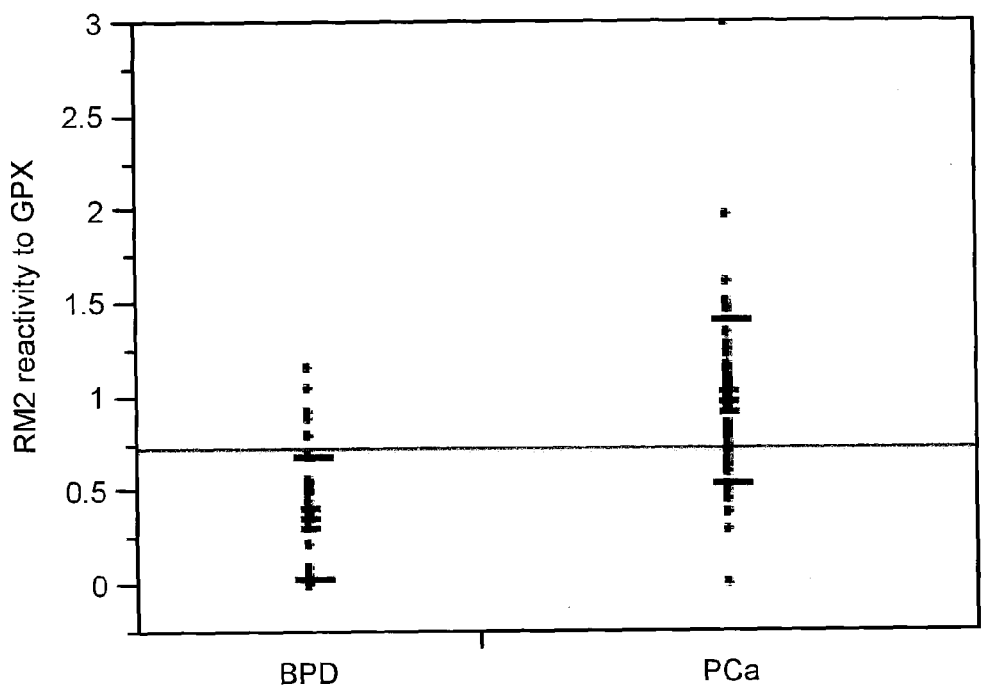
FIG. 1c is a chart showing increased RM2 reactivity to GPX in serum obtained from patients with prostate cancer compared with RM2 reactivity to GPX in patients with benign prostatic disease. A large bar represents a standard deviation and a small bar represents an average standard error.

2. Results 2.1 Reaction of Antibody RM2 to Serum of Prostate Cancer and of Benign Prostatic Disease Compared with 43 patients with benign prostatic disease, antibody RM2 reaction was enhanced on serum glycoprotein having a molecular weight of 40 kDa (designated as "GPX") in the majority of 62 patients with early prostate cancer (FIG. 1a, 1b, 4b, right). When IgM was used as a negative control, no reaction was observed in serum protein (data not shown). These patients were subjected to histological diagnosis via biopsy and exhibited PSA levels of less than 10 ng/ml. There were no significant differences between two groups in terms of age and PSA. Reaction of RM2 to GPX determined using Scion image was normalized to the reaction of RM2 to an internal control sample having a molecular weight of 75 kDa. The RM2 reaction level to GPX in the case of prostate cancer (0.96±0.43) was significantly higher than the reaction level in the case of a benign prostatic disease (0.35±0.32) (p<0.0001) (FIG. 1c).

Figure 1D:
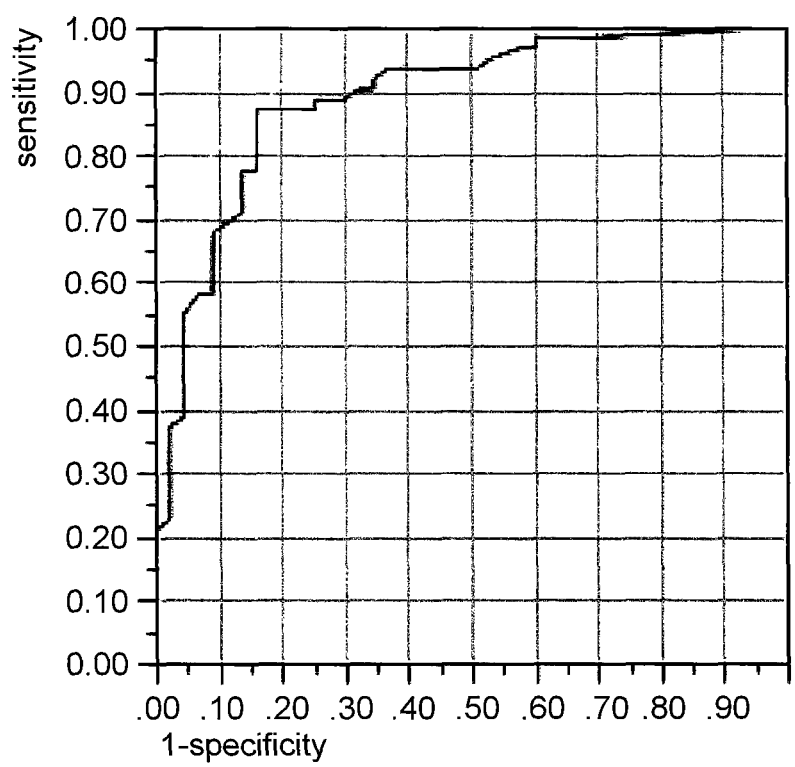
FIG. 1d shows an ROC curve of RM2 reactivity to GPX in sera obtained from patients with prostate cancer. The area under the ROC curve was 0.8874. The maximal difference in the value sensitivity—(1-specificity) was attained when the sensitivity was 87.1%.

Receiver operating characteristic (ROC) analysis was performed. As a result, the area under the ROC curve (AUC) representing the RM2 reaction to GPX was found to be as high as 0.8874. When the cut-off level of the RM2 reaction to GPX was set as 0.59, sensitivity and specificity of the RM2 reaction to GPX in prostate cancer detection were 87% and 84%, respectively (FIG. 1d).

Variables predicting the level of RM2 reactivity to GPX were explored via univariate analysis, and the RM2 reaction level to GPX was found to have no association with the pretreatment variables in 62 patients (Table 2a). Such reaction level was found to be significantly associated with the origin of major cancer among the postsurgical variables in 24 patients who had undergone radical prostatectomy (Table 2b). Specifically, cancer of transition zone origin exhibited a lower RM2 reaction level than that of peripheral zone origin.

Figure 2A:
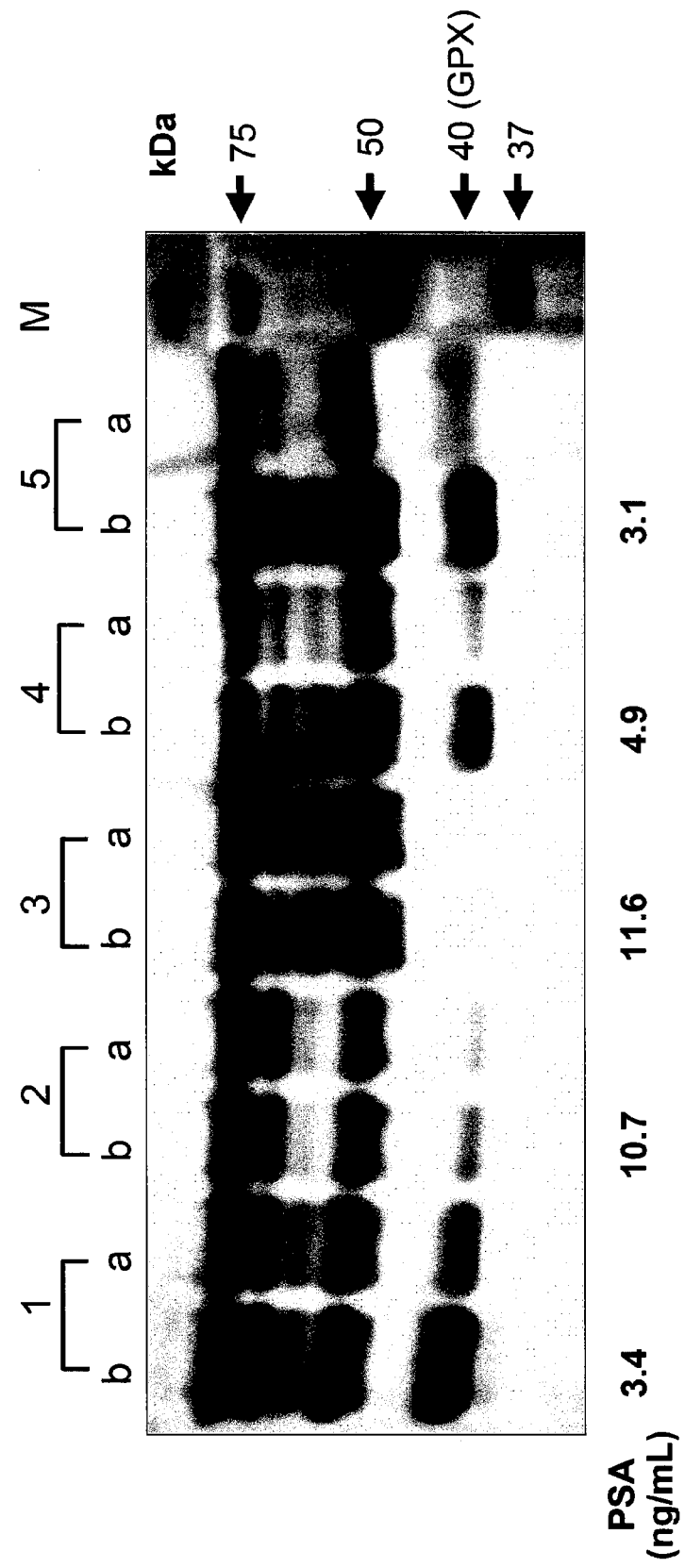
FIG. 2a is a photograph showing changes in RM2 reactivity to GPX after radical prostatectomy. Examples of RM2 reactivity to serum before and after radical prostatectomy are shown. A PSA level before surgery is shown at the lower end. All of the 5 cases exhibited the Gleason scores of 7, and the pathological T stage was 2b except for No. 5 (3a). "b" represents the data before radical prostatectomy, "a" represents the data after radical prostatectomy, and "M" represents a size marker.
Figure 2B:
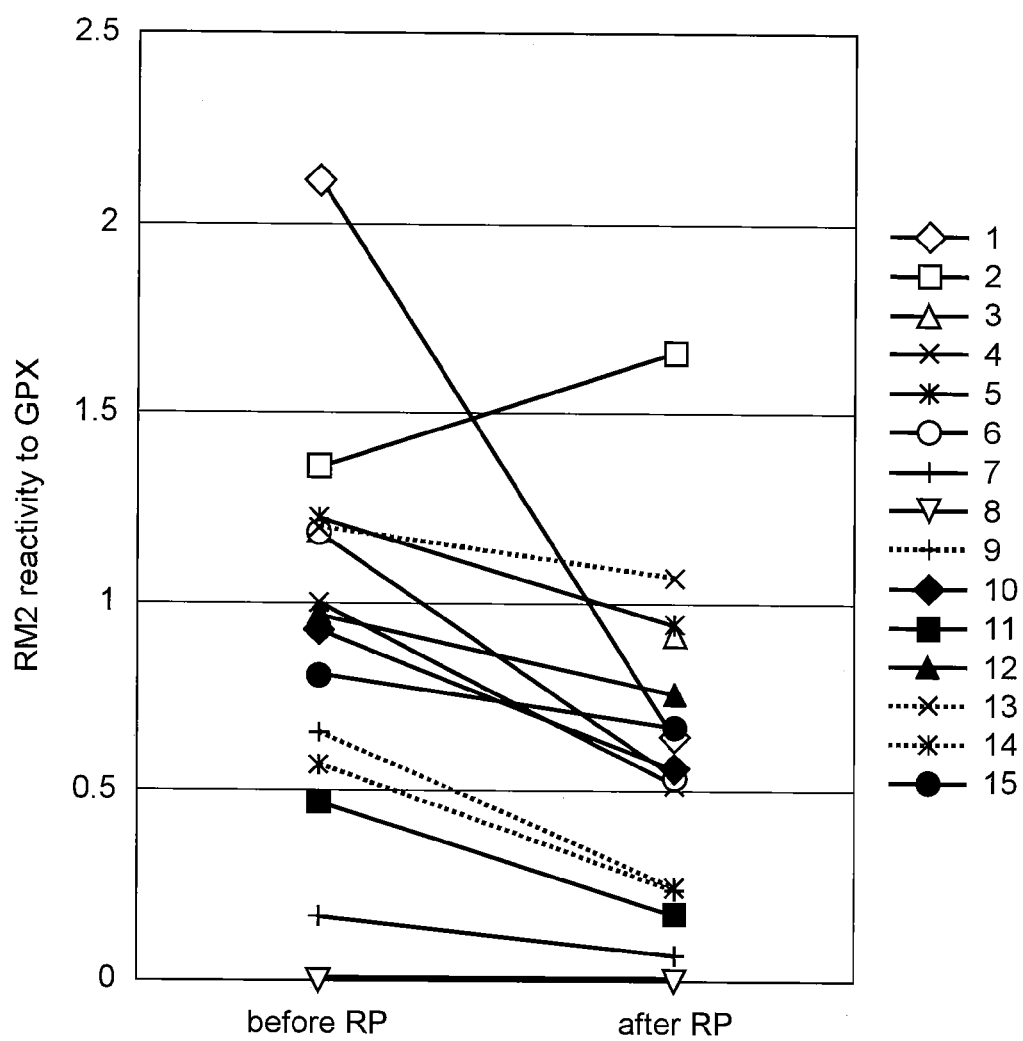
FIG. 2b is a chart showing changes in RM2 reactivity to GPX after radical prostatectomy. Changes in RM2 reactivity to GPX after radical pro statectomy of 15 cases are shown. "RP" represents radical prostatectomy.

15 patients were subjected to inspection of the reactivity of antibody RM2 to GPX before and after radical prostatectomy. These patients exhibited various preoperative PSA levels; however, their postoperative PSA levels were decreased to below 0.1 ng/ml, which is considered to be recurrence-free (Table 1c). RM2 reaction levels to GPX varied, but 13 of 15 patients showed decreased RM2 reaction levels (FIG. 2a and FIG. 2b). RM2 reaction levels were significantly decreased after radical prostatectomy (preoperative/postoperative=0.92±0.52/0.60±0.43; p=0.006) (FIG. 2b). The profiles of RM2 reaction to the sera of other genitourinary cancers were substantially the same as those to serum of prostate cancer (see Example 2), and an RM2 reaction level to GPX of 0.59 or higher was observed in 7 of 8 renal cancer cases and 2 of 8 testicular tumor cases. Regarding urothelial cancer, 37 cases were examined, and significant differences were observed in RM2 reaction level, depending on whether the cancer was a superficial cancer or invasive/advanced cancer (see Example 2). Accordingly, the antibody RM2 reaction to GPX was not specific for prostate cancer, and such reaction was also observed in the case of other genitourinary cancers.

TABLE 1

Backgrounds of patients a. Backgrounds of patients exhibiting serum PSA levels of less than 10 ng/ml having biopsy proven histological diagnosis

|     | PCa | BPD | p value |
|-----|-----|-----|---------|
| Age | 68.6 ± 6.4 | 66.8 ± 7.6 | 0.2 |
| PSA | 5.3 ± 2.1 | 5.0 ± 2.1 | 0.4 |
| F/T | 0.16 ± 0.1 | 0.22 ± 0.1 | 0.007 | b. Clinical T (primary lesion) stage and biopsy Gleason score of prostate cancer with PSA of less than 10 ng/ml

| parameters | | No. of patients |
|---|---|---|
| cT | 1b | 1 |
|    | 1c | 45 |
|    | 2a | 11 |
|    | 2b | 4 |
|    | 3a | 1 |
| bGS | 6 | 8 |
|     | 7 | 43 |
|     | 8 | 5 |
|     | 9 | 8 |

TABLE 1-continued

Backgrounds of patients c. Backgrounds of 15 cases in which RM2 reactivity before and after radical prostatectomy were compared
Age (median) 55-75 (67)
Preoperative PSA (median) 3.07-24.29 (5.41)

| Pathological parameters | | No. of patients |
|---|---|---|
| pT | 2a | 1 |
|    | 2b | 9 |
|    | 3a | 5 |
| RPGS | 5 | 1 |
|      | 7 | 13 |
|      | 8 | 1 |

PCa: prostate cancer
BPD: benign prostatic disease
F/T: ratio of free PSA to total PSA
cT: Clinical T stage
bGS: Gleason score of biopsy sample
pT: Pathological T stage
RPGS: Gleason score of radical prostatectomy sample

TABLE 2

Statistical analysis a. Correlation between pretreatment variables and RM2 reactivity

| variables | p value |
|-----------|---------|
| age | 0.1769 |
| PSA | 0.0922 |
| bGS | 0.4023 |
| cT | 0.8196 |
| No. of positive biopsy core | 0.1429 | b. Correlation between postoperative variables and RM2 reactivity

| variables | p value |
|-----------|---------|
| age | 0.0980 |
| PSA | 0.9843 |
| RPGS | 0.3723 |
| index cancer origin | 0.0117 |
| total cancer volume | 0.3433 |
| pT | 0.6099 | cT: Cinical T stage
bGS: Gleason score of biopsy sample
Number of positive needle biopsy cores
pT: pathological T stage
RPGS: Gleason score of radical prostatectomy sample
Index cancer origin (origin of major cancer)

2.2 Identification of GPX

Molecular parameters of GPX were analyzed and, molecules thereof were identified. At the outset, GPX was separated with the use of the Agilent column, and the separated GPX was then subjected to two-dimensional electrophoresis, gel digestion, HPLC, and ionization mass spectrometry. As a result, GPX was found to be the haptoglobin β chain (FIG. 3a to FIG. 3e).

Two-dimensional electrophoresis showed apparent differences in a fraction composed of 4 contiguous spots (designated as spots 1, 2, 3, and 4) between serum of a patient with cancer (specimen II-c, FIG. 3a) and serum of a patient with benign disease (specimen II-b, FIG. 3a). Differences between serum of a patient with cancer and serum of a patient with a benign disease were more distinct after performing two-dimensional electrophoresis with Western blotting using antibody RM2. Specifically, spots that were blotted with antibody RM2 were found to be strong for serum specimen II-c of prostate cancer and negative to serum specimen II-b of benign disease. The 4 contiguous spots from specimen II-c were excised, subjected to gel digestion with trypsin, and then subjected to LC-MS/MS analysis for protein identification. FIG. 3b shows an example of a peptide standard peak chromatogram of spot 2 of GPX, which had been digested with trypsin. FIG. 3c shows the results of data search via TurboSEQUEST. The results indicate that GPX is a human haptoglobin 2 precursor. Although 9 trypsin-digested peptides (sequences thereof are represented as "sequences" in the lower part of FIG. 3c by following file names, 2 of 10 sequences in total are the same sequence, the number of peptides is thus 9) were found, and these peptides corresponded to 25% coverage of the human haptoglobin precursor. However, the human haptoglobin precursor (PubMed Entry P00738, gi: 123508) is composed of a signal peptide (1 to 18 residues), the α chain (19 to 160 residues), and the β chain (162 to 406 residues). All trypsin-digested peptides were derived from the β chain. Peptide coverage for the haptoglobin β chain was 38.8% for spot 2. Peptide coverage was at similar levels for other spots, and GPX was identified as the haptoglobin β chain. Coverage for spots 1, 3, and 4 was 35.5%, 20.0%, and 35.5%, respectively. FIG. 3d shows that the MS/MS spectra of the double-charged precursor ion at the mass-to-charge ratio (m/z) of 680 is SC (PAM) AVAEYGVYVK (SEQ ID NO: 1). FIG. 3e shows that the MS/MS spectra at the mass-to-charge ratio (m/z) of 710 is DIAPTLTLYVGKK (SEQ ID NO: 2). Amino acid sequences shown in FIG. 3d and in FIG. 3e correspond to residues 380 to 391 and residues 216 to 228 of the haptoglobin precursor.

2.3 Preferential Reactivity of Antibody RM2 to Haptoglobin Chain Derived from Prostate Cancer The reaction profiles of antibody RM2 to serum were very similar to those of the anti-haptoglobin polyclonal antibody (FIG. 4a, FIG. 4b). This finding may support the results of proteomics analysis described above. Further, antibody RM2 exhibited more preferential reactivity to the haptoglobin β chain derived from cancer, compared with the haptoglobin β chain derived from benign disease (FIG. 4a, FIG. 4b, and FIG. 3a). Increased levels of haptoglobin β chain mRNA compared with human normal prostate gland epithelium PrEC were observed in LNCaP, PC3, and DU145 (the upper panel in FIG. 4c). In comparison with benign prostatic glands or stroma, elevated reactivity of the anti-haptoglobin polyclonal antibody was observed in prostate cancer cells (the lower panel in FIG. 4c). The results suggest that haptoglobin β chains vary quantitatively and qualitatively between a patient with prostate cancer and a patient with benign prostatic disease.

3. Discussion

The monoclonal antibody RM2 was originally established for disialoganglioside and found later to recognize the sugar chain antigen ((β1,4-GalNAc-disialyl Lc4). The present inventors discovered that antibody RM2 would also react with the haptoglobin β chain. Further, antibody RM2 was found to more preferentially react with the haptoglobin β chain derived from serum of a patient with prostate cancer. It is suggested that qualitative changes in the haptoglobin β chain, in addition to quantitative changes thereof, would produce significant differences in RM2 reactions between prostate cancer and benign prostatic disease.

Based on the findings of the present inventors, status of a sugar chain of serum haptoglobin β chain was inspected. As a result, the present inventors discovered that the haptoglobin β chain has very small amounts of O-linked sugar chains, in addition to four N-linked sugar chains, and that there are differences in sugar chain statues of the haptoglobin chain between prostate cancer and benign prostatic disease.

However, the sugar chain antigen (antigen RM2: (β1,4-GalNAc-disialyl Lc4) that is recognized by antibody RM2 was not detected on the N-linked sugar chain of the haptoglobin β chain.

This indicates that preferential reactivity of antibody RM2 to serum haptoglobin chain derived from prostate cancer may be as follows. First of all, the monoclonal antibody RM2 undergoes cross reaction with a sugar chain other than β1,4-GalNAc-disialyl Lc4. In the second place, an antibody may react with structural changes in the haptoglobin β chain that may be caused by sugar chain addition. In the third place, multiple reactivity of a monoclonal antibody, which has become elucidated recent years, that is, the possibility such that a monoclonal antibody would bind to a large and complicated molecule that is completely unrelated to a target molecule in terms of structure may be considered. A monoclonal antibody that recognizes disialoganglioside, such as GD3 also reacts with, for example, actin, thyroglobulin, ssDNA, and dsDNA. In particular, a monoclonal antibody of isotype IgM often shows multidimensional reactivity. Antibody RM2 is of the IgM class, and reactivity of antibody RM2 to the haptoglobin β chain may be described in terms of multidimensional reactivity.

In any case, the level of the haptoglobin β chain defined by antibody RM2 was found to significantly increase in the case of prostate cancer. Increase in RM2 reactivity was also observed in other urinary cancers.

Thus, antibody RM2 can be useful for detecting early prostate cancer as an auxiliary marker of PSA as an organ-specific marker.

According to the present invention, the haptoglobin level was found to quantitatively increase in the case of prostate cancer, compared with normal prostate gland epithelial cells, via RT-PCR or immunohistochemical staining, and qualitative differences in the haptoglobin chain between prostate cancer and benign prostatic disease were observed via Western blotting. Qualitative differences in haptoglobin were also shown in the case of head and neck cancer. While haptoglobin derived from serum of a patient with cancer exhibits immune suppression, that of the normal serum did not exhibit immune suppression.

As described above, quantitative and qualitative changes in the haptoglobin β chain were found to serve as useful indicators for early diagnosis or prediction of prognosis of genitourinary cancers, including prostate cancer. It was also suggested that such changes can be used as the markers for early diagnosis or prediction of prognosis of other cancers.

Example 2

Reaction of Antibody RM2 to Serum of Patient with Urothelial Cancer

1. Subjects and Method

Serum samples were obtained from 37 urothelial cancer subjects (i.e., 26 subjects with bladder cancer and 11 subjects with cancer of the renal pelvis and ureter; all subjects were males). The average age was 65.2±10.9. The reaction of antibody RM2 to serum was assayed and quantitative assay were carried out in the same manner as in Example 1.

2. Results

Significant differences were observed in reaction of antibody RM2 to the haptoglobin β chain, depending on whether a case was of superficial cancer (invasion was up to the submucosal layer; n=18), muscle invasive cancer (muscle invasion; n=16), or advanced cancer (urothelial cancer with inoperable topical invasion or metastasis; n=3) (FIG. 5). Specifically, RM2 reaction levels were significantly increased in the case of muscle invasive cancer and advanced cancer (RM2 reaction (the value normalized to RM2 reaction to 75 kDa protein): superficial cancer 0.31±0.33; muscle invasive/advanced cancer 0.96±0.49, p<0.0001) (FIG. 6).

3. Discussion

Since there has been no serum marker useful for detecting urothelial cancer in the past, the present inventors demonstrated that the haptoglobin β chain to which antibody RM2 specifically binds was a non-specific cancer marker, but it can be useful for objectively evaluating the progress of urothelial cancer. Since muscle invasive cancer is generally equivalent to grade 3 urothelial cancer, that is, muscle invasive cancer is highly malignant. This can be useful when more appropriate treatment is to be provided to a patient with urothelial cancer. Further, this can be useful as a means for finding residual or recurrence of cancer after surgery in a non-invasive manner. Thus, it can be useful for application of postoperative auxiliary chemotherapy or checking of recurrence at an early stage.

Example 3

Differences in Recurrence-Free Rate of Prostate Cancer after Radical Prostatectomy Based on the Different Levels of Haptoglobin β Chains Defined by Antibody RM2

1. Definition

The term "PSA recurrence" is used when prostate cancer is treated via radical prostatectomy or other means, the serum PSA level is thereby reduced to a normal range, and the serum PSA level exceeds the specified level again. "PSA recurrence" is a very early stage of prostate cancer recurrence that cannot be detected via imagings such as CT or MRI, and it is also referred to as "biochemical recurrence." If PSA recurrence remains uncontrolled, PSA would eventually advance to mass formation at a topical region (i.e., a site where the prostate gland was removed) or bone metastasis that can be detected by the imagings, which is referred to as a "clinical recurrence."

2. Subjects and Method

Among 62 patients with prostate cancer who had been subjected to the inspection of the RM2 reaction level to the haptoglobin β chain, 24 patients who had undergone radical prostatectomy were inspected regarding differences in the rate of PSA recurrence based on the different RM2 reaction levels. In this example, the date of PSA recurrence was defined at when serum PSA level exceeded 0.1 ng/ml, and if serum PSA level did not fall to 0.1 ng/ml or lower after surgery it was defined as at the time of operation.

The RM2 reaction level in the case of prostate cancer was quantified by the method described in 1-(4) of Example 1.

3. Results

The results are shown in FIG. 7. The vertical axis represents the rate of PSA non-recurrence and the horizontal axis represents the duration of observation (unit: month). Since the average RM2 reaction level in the case of prostate cancer was 0.96, the values were classified as "higher than 0.96 (>0.96)" and "lower than 0.96 (<0.96)," and the rate of PSA non-recurrence was calculated by the Kaplan-Meier curve. As a result, the >0.96 cases (11 cases) were found to exhibit a lower rate of PSA non-recurrence than the <0.96 cases (13 cases). The Log-rank test yielded a difference of p=0.0527, which was substantially significant. Accordingly, the level of the haptoglobin β chain defined by antibody RM2 was found to serve as a factor for predicting PSA recurrence after radical prostatectomy. Specifically, it was suggested that the level of serum haptoglobin β chain defined by antibody RM2 would reflect the grade of malignancy of early prostate cancer.

Example 4

Evaluation of Expression of Ganglioside β1,4-GalNAc-disialyl Lc4 that is Recognized by Antibody RM2 in Prostate Cancer Cell Line 1. Material and Method The established prostate cancer cells that were used for glycolipid extraction were PC3, LNCaP, AICaP1 (the androgen-independent prostate cancer cell lines that were newly established in the Department of Urology, Tohoku University School of Medicine), and the renal cancer cell line (TOS1; the renal cancer cell line that had been previously established in the Department of Urology, Tohoku University School of Medicine). Glycolipid extraction was carried out in the following manner. The cell lines ($3\times10^7$ cells, equivalent to about 200 mg) were collected via centrifugation, 2 ml of a mixed solution of isopropanol/hexane/water (55:25:20, v/v/v) was added thereto, and extraction was carried out twice. The obtained extracts were combined and concentrated to dryness by a nitrogen purge. Subsequently, phospholipids in the dry product were dissolved in 2 ml of a methanol solution containing 0.1M NaOH, and the solution was maintained at 40° for 2 hours for hydrolysis, followed by neutralization with 2000 of 1N hydrochloric acid. The generated fatty acid was removed by repeated hexane extraction (2 ml/extraction). Glycolipids in a lower phase were demineralized and purified using the SepPak C18 cartridge (Millipore). The recovered total glycolipids were lyophilized and redissolved in a mixed solution of chloroform/methanol (2:1). The cell lines (15 mg equivalent) were spotted on TLC (Merck) and developed with the aid of a mixed solution of chloroform/methanol/0.5% aqueous $CaCl_2$ solution (50:40:10). The TLC plate was air-dried, immersed in 0.5% polyisobutyl methacrylate dissolved in hexane/chloroform (9:1) for 1 minute, and blocked by immersing the plate in a PBS solution containing 3% bovine serum albumin at room temperature for 1 hour. After TLC was mildly washed with PBS, antibody RM2 (the primary antibody) was allowed to react therewith for 2 hours, the horseradish peroxidase-labeled rabbit anti-mouse IgM antibody (Zymed) (the secondary antibody) was allowed to react therewith for 1 hour, and detection was then carried out using Konica immunostain HRP-1000 (Konica).

2. Results

The results are shown in FIG. 8. Glycolipids extracted from 15 mg each of prostate cancer cells PC3, LNCaP, and AICaP1 were spotted on TLC, and detection was carried out via immunostaining using antibody RM2. As a result, antibody RM2 was found to react preferentially with TOS1 (a positive control) in which β1,4-GalNAc-disialyl Lc4 (GalNAcD-SLc4) expression was observed, and no band was observed in any of the prostate cancer cell lines. It was thus considered that, in these prostate cancer cells, β1,4-GalNAc-disialyl Lc4, which is ganglioside recognized by antibody RM2, is not expressed or the expression level thereof is lower than the detection limit. Also, β1,4-GalNAc-disialyl Lc4 was not detected in the culture supernatant of any of such prostate cancer cell lines and TOS1 (data not shown).

Example 5

Changes in RM2 Reactivity Via Treatment with Hemoglobin Column

In Example 1, the RM2-reactive protein was demonstrated to be the haptoglobin β chain as a result of ionizing mass spectrometry. In this experiment, with the utilization of properties of haptoglobin that adsorbs to hemoglobin, the cell extract of the prostate cancer cell line DU145 was subjected to hemoglobin column treatment, the sample was subjected to electrophoresis before and after the treatment, and behavior of the RM2-reactive protein was inspected via Western blotting to verify that the RM2-reactive protein was haptoglobin.

1. Material and Method
(1) Preparation of Hemoglobin Column

Human hemoglobin, which was purified via weak anion exchange resin (DEAE resin), was purchased from Sigma. CNBr-activated Sepharose (5 g, dry weight, GE Healthcare Biosciences) was swollen and washed three times with a 1 mM HCl solution. Subsequently, gel was washed with an immobilization solution (a 0.1 M $NaHCO_3$ solution containing 0.5 M NaCl, pH 8) and resuspended in the solution (about 25 ml) for deaeration. A hemoglobin solution (2 ml; concentration: 25 mg/ml) that had been previously dialyzed against the immobilization solution was added thereto, and the mixture was allowed to react at room temperature for 1 hour. After the reaction, the gel was washed three times with the immobilization solution (200 ml in total). Unreacted active groups were allowed to react with the aid of 0.1M Tris-HCl buffer (pH 8.0) for 2 hours and then blocked. The percentage of hemoglobin immobilization was 98%. The hemoglobin-immobilized gel suspension was deaerated, a column (1.5 cm (I.D.)×20 cm) was filled with the resultant, and a step of washing with a PBS solution (0.15 M NaCl, 20 mM $Na_2HPO_4/NaH_2PO_4$, pH 7.2) and with a 0.15 M NaCl solution (pH 11) was repeated two times, followed by equilibration with a PBS solution.

(2) Column Procedure

The DU145 cell extract (100 μl) was applied to the column filled with the hemoglobin-immobilized carrier, PBS was flushed through the column as an eluant, and a fraction that had passed through the column was recovered during UV observation at 280 nm (lane 2, without incubation). Similarly, 100 μl of the DU145 cell extract was subjected to a batch reaction with the hemoglobin-immobilized carrier at 4° C. for 24 hours, an empty column was filled with the reaction product, the column was allowed to stand for 5 minutes, PBS was flushed through the column, and a fraction that had passed through the column was recovered in the same manner (lane 3). The hemoglobin-immobilized column was washed with PBS, and the adsorbed fraction was then eluted with the aid of a 0.15 M NaCl solution (pH 11) (lane 4). The recovered fractions were demineralized, concentrated in vacuo, dissolved in 50 μl of a sample buffer, boiled for 5 minutes, subjected to SDS-PAGE, and then subjected to Western blot analysis in accordance with a conventional technique using antibody RM2. An untreated cell extract was used as a positive control (lane 1).

2. Results

The results are shown in FIG. 9. Lane 1 shows untreated DU145 cell extract, lane 2 shows a fraction of the DU145 cell extract that had passed through the hemoglobin column without incubation, lane 3 shows a fraction of the DU145 cell extract that had passed through the hemoglobin column after incubation for 24 hours, and lane 4 shows a PBS elution fraction from the column after incubation. Compared with the control, a band intensity corresponding to the molecular weight of the haptoglobin β chain (40 kDa) and that of the haptoglobin α- and β-chain complex (50 kDa) was weaker in lane 2. As shown in lane 3, the sample that had been subjected to the reaction for 24 hours showed a further weakened band. This indicates that reactivity of antibody RM2 to a fraction that is considered to be the haptoglobin β chain (40 kDa) and that of the haptoglobin α- and β-chain complex (50 kDa) is substantially lost (lane 3). The fraction that had been recovered by subjecting the haptoglobin-immobilized carrier column after 24-hour-reaction to elution with PBS showed reactivity to antibody RM2 (lane 4). These results strongly suggest that the RM2-reactive antigen that is present in the DU145 cell is haptoglobin. According to immunostaining analysis using TLC of the ganglioside fractions extracted from the established prostate cancer cells (PC3, LNCaP, and AICaP1) and the renal cancer cell line (TOS1), reactivity of antibody RM2 was observed only in a positive control (TOS1), as shown in FIG. 8. β1,4-GalNAc-disialyl Lc4 that is recognized by antibody RM2 was not detected in the culture supernatant of any of the prostate cancer cell lines and TOS1. Based on such results, the possibility such that ganglioside that is recognized by antibody RM2 is released from the cancer cell to serum, that it is bound to the haptoglobin β chain, and that the resultant is recognized by antibody RM2 may be rejected. RM2 reactions to the prostate cancer cells are considered to depend mostly on the structure of sugar chains other than RM2 antigen added to the haptoglobin β chain or structural changes in the haptoglobin β chain resulting from sugar chain addition.

Example 6

Changes in RM2 Reactivity by Treatment of Serum Haptoglobin β with Enzyme

1. Material and Method

Sera of patients with prostate cancer and patients with prostate hyperplasia exhibiting PSA levels of 2.1 to 4.8 ng/ml were subjected to SDS-PAGE, and proteins were transferred onto a PVDF membrane in accordance with a conventional technique. The membranes to which proteins were transferred (3 membranes were prepared) were subjected to blocking with the use of a 1% bovine serum albumin solution at room temperature for 2 hours, and then washed with a PBS solution containing 0.05% Tween 20. After washing, the membranes were placed into plastic bags, 2 U of β-hexosaminidase from jack bean (Sigma) was added to one of the bags, and the reaction was allowed to proceed therein at 37° C. overnight. To another bag, 25 mU of sialidase from Newcastle disease virus (Glyko) was added and the reaction was allowed to proceed at 37° C. overnight. A further bag was subjected to treatment with β-hexosaminidase from jack bean (37° C. overnight), 25 mU of sialidase from Newcastle disease virus (Glyko) was added, and the reaction was allowed to proceed at 37° C. overnight. A control membrane (untreated) was subjected to the reaction with an enzyme-free solution and treated in the manner as described above. Membranes were washed with a PBS solution containing 0.05% Tween 20 and subjected to Western blot analysis in accordance with a conventional technique using antibody RM2.

2. Results

The results are shown in FIG. 10. Lanes 1 to 4 show sera obtained from patients with prostate cancer and lanes 5 to 8 show sera obtained from patients with prostate hyperplasia. "a" shows untreated serum, "b" shows serum treated with β-hexosaminidase from jack bean, and "c" shows serum treated with β-hexosaminidase and then with sialidase from Newcastle disease virus. RM2 reaction levels were not lowered via single treatment (panel b; sialidase treatment alone provides the same results as "b" and thus is not shown). When treated with β-hexosaminidase from jack bean and then with sialidase from Newcastle disease virus, RM2 reaction to 40 kDa (the haptoglobin β chain) is substantially lost. Whether antibody RM2 recognizes structural changes, which are secondarily induced by a sugar chain, or sugar chain structure itself is unknown. However, it is certain that sugar chain addition to the haptoglobin chain is associated with the reaction of antibody RM2 to the haptoglobin chain.

Example 7

ELISA Using Antibody RM2

1. Material and Method

The goat anti-mouse IgM antibody (KPL) was diluted to 5 μg/ml with PBS, dispensed in amounts of 100 μl on a 96-well plate for ELISA (Falcon), and the antibody was adsorbed to the plate at 4° C. overnight. After being washed twice with a PBS solution containing 0.05% Tween 20, 100 μl of a PBS solution containing antibody RM2 at 5 μg/ml was added to each well, and the reaction was allowed to proceed at 37° C. for 1 hour. After being washed twice with a PBS solution containing 0.05% Tween 20, 200 μl of a PBS solution containing 1% BSA was added to each well, followed by blocking. Subsequently, the plate was washed twice with a PBS solution containing 0.05% Tween 20, 100 μl of a PBS-diluted specimen (8 μl of the specimen and 92 μl of PBS) was added thereto, and the reaction was allowed to proceed at 37° C. for 1 hour. The plate was washed 5 times with a PBS solution containing 0.05% Tween 20, 100 μl of the rabbit anti-haptoglobulin polyclonal antibody (Dako) diluted 1,000-fold with a PBS solution containing 0.1% BSA was added, and the reaction was allowed to proceed at 37° C. for 1 hour. The plate was washed 5 times with a PBS solution containing 0.05% Tween 20, and reacted with 100 μl of the horseradish peroxidase-labeled anti-rabbit antibody (Santa cruz) diluted 1,000-fold at 37° C. for 1 hour. The horseradish peroxidase substrate TMB solution (T8665, Sigma) was added at 100 μl/well, the reaction was allowed to proceed at room temperature for 5 minutes, 100 μl of a reaction terminator (0.5M-$H_2SO_4$) was added, and the absorbance at 450 nm was measured.

2. Results

The results are shown in FIG. 11. 12 serum samples obtained from patients with prostate cancer and 12 serum samples obtained from patients with benign prostatic disease were subjected to ELISA. As a result, the average±the standard deviation value of the 12 measured serum samples of the patients with benign prostatic disease was 0.58±0.48, and that of the 12 measured serum samples of the patients with prostate cancer was as high as 1.1±0.64 (P=0.0352). This demonstrates a significant difference in reactivity.

Example 8

Western Blot Analysis of Urine Samples Obtained from Patients with Urothelial Cancer Using Antibody RM2

1. Material and Method
(1) Western Blotting of Urine Samples

To urine samples (40 μl each) obtained from patients with urothelial cancer (i.e., 3 patients with bladder cancer and 2 patients with renal pelvic cancer and bladder cancer) and from 2 healthy individuals, 10 μl of 5× sample buffer (125 mM Tris-HCl, 25% glycerol, 5% SDS, 0.5% bromophenol blue, 5% 2-mercaptoethanol, pH 6.5) was added, the mixtures were boiled for 5 minutes, 20 to 30 μl thereof was subjected to electrophoresis on 10% SDS-polyacrylamide, and proteins in the gel were transferred to the Hybond P PVD membrane via electroblotting at 15 V for 45 minutes. The resultants were washed with a TBST solution (50 mM Tris-HCl, 0.15 M NaCl, 0.05% Tween 20, pH 7.6) at room temperature for 10 minutes, followed by blocking with a TBST solution containing 1% BSA at 37° C. for 30 minutes. The membrane was introduced into a plastic bag, antibody RM2 diluted with a TBST solution (final concentration: 10 μg/ml) was added thereto, and the reaction was allowed to proceed at 4° C. overnight. The membrane was washed with a TBST solution for 10 minutes three times in total. After the 4,000-fold diluted horseradish peroxidase-labeled rabbit anti-mouse IgM antibody (Zymed) was allowed to react at 37° C. for 30 minutes, the membrane was washed with a TBST solution for 10 minutes three times in total. Proteins that had reacted with antibody RM2 were subjected to chemoluminescence with the use of the ECLPlus kit (GE Healthcare Biosciences), and imaged using VersaDoc 3000 (Bio-Rad).

2. Results

The results of Western blot analysis using antibody RM2 are shown in FIG. 12. Lanes 1 to 3 show the results for patients with bladder cancer, lanes 4 and 5 show the results for patients with renal pelvic cancer and bladder cancer, and lanes 6 and 7 show the results for healthy individuals. In 3 of 5 urothelial cancer cases, bands of about 75 kDa positive for antibody RM2 were detected. No reaction to antibody RM2 was observed in two healthy individuals.

INDUSTRIAL APPLICABILITY

According to the present invention, early diagnosis or prediction of prognosis of genitourinary cancers, including prostate cancer, can be accomplished in a simple and non-invasive manner with the use of sera of patients or the like.

The present invention can be extensively utilized in medical and pharmaceutical fields, such as for early diagnosis or prediction of prognosis of genitourinary cancers, including prostate cancer, for development of a therapeutic agent therefor, and for other purposes.

All publications, patents, and patent applications cited herein are incorporated herein by reference in their entirety.

SEQUENCE LISTING FREE TEXT

SEQ ID NO: 1; synthetic peptide (residues 380-391 of the haptoglobin precursor)

SEQ ID NO: 2; synthetic peptide (residues 216-228 of the haptoglobin precursor)

---

The invention claimed is:

1. A method for evaluating a risk, prognosis, or grade of malignancy of genitourinary cancer in a subject, comprising:
isolating tissue, body fluid or excretory substance from the subject to obtain isolated tissue, body fluid or excretory substance,
contacting said tissue, body fluid or excretory substance with antibody RM2,
detecting binding of said antibody RM2 to a haptoglobin β chain in said tissue, body fluid or excretory substance, and
determining an elevated risk, prognosis or grade of malignancy of genitourinary cancer in the subject when a level of the haptoglobin β chain or a fragment thereof to which antibody RM2 specifically binds is significantly higher in the subject compared to a healthy subject.

2. The method according to claim 1, wherein said antibody RM2 does not bind to the haptoglobin β chain or a fragment thereof via a sugar chain β1,4-GalNAc-disialyl Lc4.

3. The method according to claim 1, wherein the genitourinary cancer is selected from the group consisting of prostate cancer, renal cancer, urothelial cancer, and testicular cancer.

4. The method according to claim 1, wherein the genitourinary cancer is prostate cancer.

5. The method according to claim 1, wherein said tissue, body fluid or excretory substance of said subject is serum of said subject.

6. The method according to claim 1, wherein the level of the haptoglobin β chain or a fragment thereof to which antibody RM2 specifically binds is determined by (i) mass spectrometry selected from SELDI-TOF-MS and MALDI-TOF-MS, or (ii) immunological techniques selected from solid phase immunoassay including Western blotting, dot blotting, slot blotting, ELISA, RIA, and immunoprecipitation assay techniques.

7. The method according to claim 6, wherein the level of the haptoglobin β chain or a fragment thereof to which antibody RM2 specifically binds is determined via SELDI-TOF-MS, MALDI-TOF-MS, or ELISA.

8. The method according to any one of claims 1 to 7, further comprising:
determining presence of an organ-specific cancer marker.

9. The method according to claim 8,
wherein said genitourinary cancer is prostate cancer, and
wherein the organ-specific marker is PSA.

10. A method for evaluating a risk, prognosis, or grade of malignancy of genitourinary cancer in a subject, comprising:
determining an elevated risk, prognosis or grade of malignancy of genitourinary cancer in the subject when a level of the haptoglobin β chain or a fragment thereof to which antibody RM2 specifically binds is significantly higher in the subject compared to a healthy subject, the level of the haptoglobin β chain or a fragment thereof to which antibody RM2 specifically binds having been determined by isolating tissue, body fluid or excretory substance from the subject to obtain isolated tissue, body fluid or excretory substance, contacting said tissue, body fluid or excretory substance with antibody RM2 and detecting binding of said antibody RM2 to a haptoglobin β chain in said tissue, body fluid or excretory substance.

11. A method for evaluating a risk, prognosis, or grade of malignancy of genitourinary cancer in a subject, comprising:
isolating tissue, body fluid or excretory substance from the subject to obtain isolated tissue, body fluid or excretory substance,
contacting said tissue, body fluid or excretory substance with antibody RM2, and
detecting binding of said antibody RM2 to a haptoglobin β chain in said tissue, body fluid or excretory substance,
wherein an elevated risk, prognosis or grade of malignancy of genitourinary cancer is determined in the subject when a level of the haptoglobin β chain or a fragment thereof to which antibody RM2 specifically binds is significantly higher in the subject compared to a healthy subject.

12. A method for evaluating a risk, prognosis, or grade of malignancy of genitourinary cancer in a subject, comprising:
contacting tissue, body fluid or excretory substance with antibody RM2, said tissue, body fluid or excretory substance having been isolated from the subject,
detecting binding of said antibody RM2 to a haptoglobin β chain in said tissue, body fluid or excretory substance, and
determining an elevated risk, prognosis or grade of malignancy of genitourinary cancer in the subject when a level of the haptoglobin β chain or a fragment thereof to which antibody RM2 specifically binds is significantly higher in the subject compared to in a healthy subject.

13. The method according to claim 1, wherein the level of the haptoglobin β chain or a fragment thereof to which antibody RM2 specifically binds is detected using a sandwich ELISA assay.

14. The method according to claim 10, wherein the level of the haptoglobin β chain or a fragment thereof to which antibody RM2 specifically binds is detected using a sandwich ELISA assay.

15. The method according to claim 11, wherein the level of the haptoglobin β chain or a fragment thereof to which antibody RM2 specifically binds is detected using a sandwich ELISA assay.

16. The method according to claim 12, wherein the level of the haptoglobin β chain or a fragment thereof to which antibody RM2 specifically binds is detected using a sandwich ELISA assay.

17. The method according to claim 1, wherein said tissue, body fluid or excretory substance of said subject is blood of said subject.

18. The method according to claim 1, wherein said tissue, body fluid or excretory substance of said subject is urine or tissue extract of said subject.

19. The method according to claim 1, wherein said tissue, body fluid or excretory substance of said subject is sputum or stool of said subject.

20. The method according to claim 10, wherein said tissue, body fluid or excretory substance of said subject is serum of said subject.

21. The method according to claim 10, wherein said tissue, body fluid or excretory substance of said subject is blood of said subject.

22. The method according to claim 10, wherein said tissue, body fluid or excretory substance of said subject is urine or tissue extract of said subject.

23. The method according to claim 10, wherein said tissue, body fluid or excretory substance of said subject is sputum or stool of said subject.

24. The method according to claim 11, wherein said tissue, body fluid or excretory substance of said subject is serum of said subject.

25. The method according to claim 11, wherein said tissue, body fluid or excretory substance of said subject is blood of said subject.

26. The method according to claim 11, wherein said tissue, body fluid or excretory substance of said subject is urine or tissue extract of said subject.

27. The method according to claim 11, wherein said tissue, body fluid or excretory substance of said subject is sputum or stool of said subject.

28. The method according to claim 12, wherein said tissue, body fluid or excretory substance of said subject is serum of said subject.

29. The method according to claim 12, wherein said tissue, body fluid or excretory substance of said subject is blood of said subject.

30. The method according to claim 12, wherein said tissue, body fluid or excretory substance of said subject is urine or tissue extract of said subject.

31. The method according to claim 12, wherein said tissue, body fluid or excretory substance of said subject is sputum or stool of said subject.

\* \* \* \* \*